(12) United States Patent
Traverse et al.

(10) Patent No.: US 9,133,161 B2
(45) Date of Patent: Sep. 15, 2015

(54) PROCESSES FOR PREPARING ISOINDOLINE-1,3-DIONE COMPOUNDS

(71) Applicant: Celgene Corporation, Summit, NJ (US)

(72) Inventors: John F. Traverse, Union, NJ (US); Gregg Brian Feigelson, Orange, NY (US); Alexander L. Ruchelman, Cream Ridge, NJ (US); Jihong Liu, Shanghai (CN); Hongfeng Liu, Shanghai (CN); Chengjun Ma, Shanghai (CN); Danyang Liu, Shanghai (CN); Shunxiang Zhang, Shanghai (CN)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 13/952,400

(22) Filed: Jul. 26, 2013

(65) Prior Publication Data
US 2014/0031552 A1 Jan. 30, 2014

Related U.S. Application Data

(60) Provisional application No. 61/676,759, filed on Jul. 27, 2012.

(51) Int. Cl.
C07D 401/04 (2006.01)
(52) U.S. Cl.
CPC .................................. C07D 401/04 (2013.01)
(58) Field of Classification Search
CPC ..................................................... C07D 401/04
USPC .................................. 546/200, 201; 548/479
See application file for complete search history.

(56) References Cited

U.S. PATENT DOCUMENTS

| 5,189,419 | A | * | 2/1993 | Lyden | 341/143 |
| 5,635,517 | A | | 6/1997 | Muller et al. | |
| 6,395,754 | B1 | | 5/2002 | Muller et al. | |
| 7,153,867 | B2 | * | 12/2006 | Shah et al. | 514/323 |
| 7,629,360 | B2 | | 12/2009 | Muller et al. | |
| 7,863,451 | B2 | * | 1/2011 | Muller et al. | 546/201 |
| 7,994,327 | B2 | | 8/2011 | Ge et al. | |

FOREIGN PATENT DOCUMENTS

WO 03/014315 A2 2/2003

OTHER PUBLICATIONS

Braga et al. "Making crystals . . . " Roy. Soc. Chem. Chem. Commun. p. 3635-3645 (2005).*
Dean "Analytical Chemistry handbook" p. 10.24-10.26 (1995).*
Invanisevic et al. "uses of x-ray powder . . . " Pharm. Sci. Encyclopedia p. 1-42 (201 O).*
Seddon "pseudopolym . . . " Crystal growth & design v.4(6) 1087 (2004).*
Tung et al, "Polymorphism" Cryst. Org. Compounds, p. 49 (2009).*
Vippagunta et al. "Crystalline solids" adv. Drug. Del. Rev. v.48, p. 3-26 (2001).*
Grewe "The iodomethoxyphthalic . . . " CA32:33016 (1938).*
Sureshbabu et al. "Protection reactions" Amino Acids Peptides and proteins in org. chem. p. 1-95 (2011).*
Wilds and Djerassi, "The preparation of 5-methoxybenzene-1,2,3-tricarboxylic acid," J. Am. Chem. Soc. 1946, 68, 1862-1864.

* cited by examiner

*Primary Examiner* — Celia Chang
(74) *Attorney, Agent, or Firm* — Jones Day

(57) ABSTRACT

Provided herein are processes for preparing an isoindoline-1,3-dione compound, or an enantiomer or a mixture of enantiomers thereof; or a pharmaceutically acceptable salt, solvate, hydrate, or polymorph thereof.

11 Claims, No Drawings

1

PROCESSES FOR PREPARING ISOINDOLINE-1,3-DIONE COMPOUNDS

I. CROSS REFERENCE TO RELATED APPLICATION

This application claims the benefit of U.S. Provisional Application No. 61/676,759, filed Jul. 27, 2012; the disclosure of which is incorporated herein by reference in its entirety.

II. FIELD

Provided herein are processes for preparing an isoindoline-1,3-dione compound, or an enantiomer or a mixture of enantiomers thereof; or a pharmaceutically acceptable salt, solvate, hydrate, or polymorph thereof.

III. BACKGROUND

Many types of cancers are associated with new blood vessel formation, a process known as angiogenesis. Several mechanisms involved in tumor-induced angiogenesis have been elucidated. The most direct of these mechanisms is the secretion by the tumor cells of cytokines with angiogenic properties, including tumor necrosis factor α (TNF-α).

A variety of other diseases and disorders are also associated with or characterized by undesired angiogenesis. For example, enhanced or unregulated angiogenesis has been implicated in a number of diseases and medical conditions, including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to, diabetic retinopathy, retinopathy of prematurity, corneal graft rejection, neovascular glaucoma, retrolental fibroplasia, arthritis, and proliferative vitreoretinopathy.

Certain isoindole-1,3-dione compounds, e.g., 4-amino-2-(2,6-dioxopiperidine-3-yl)isoindoline-1,3-dione, have been reported to be capable of controlling angiogenesis or inhibiting the production of TNF-α, and useful in the treatment and prevention of various diseases and conditions. See U.S. Pat. No. 5,635,517, the disclosure of which is incorporated herein by reference in its entirety.

Processes for preparing certain isoindoline-1,3-dione compounds have been described, for example, in U.S. Pat. Nos. 5,635,517; 6,395,754; and 7,994,327; the disclosure of each of which is incorporated herein by reference in its entirety. A need still exists for efficient processes for preparing isoindoline-1,3-dione compounds.

IV. SUMMARY

Provided herein is a process for preparing a compound of Formula I:

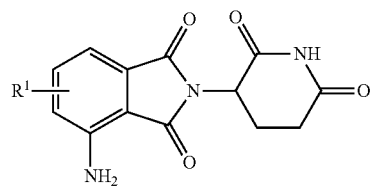

or an enantiomer or a mixture of enantiomers thereof; or a pharmaceutically acceptable salt, solvate, hydrate, or polymorph thereof;

comprising the step of reacting a compound of Formula Ia:

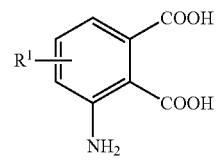

with 3-aminopiperidine-2,6-dione, or an enantiomer or a mixture of enantiomers thereof; or a salt thereof; to form the compound of Formula I;

wherein $R^1$ is hydrogen, hydroxyl, or —$OR^{1a}$; and $R^{1a}$ is a hydroxyl protecting group.

Also provided herein is a process for preparing a compound of Formula I:

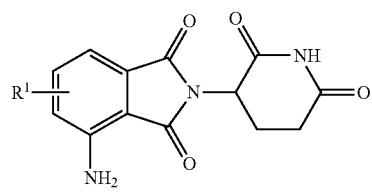

or an enantiomer or a mixture of enantiomers thereof; or a pharmaceutically acceptable salt, solvate, hydrate, or polymorph thereof;

comprising the steps of:

(i) reacting a compound of Formula IIa:

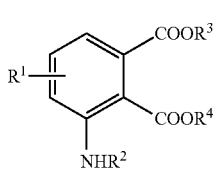

wherein:

$R^2$ is an amino protecting group; and $R^3$ and $R^4$ are each independently hydrogen or a carboxyl protecting group; with 3-aminopiperidine-2,6-dione, or an enantiomer or a mixture of enantiomers thereof; or a salt thereof; to form a compound of Formula II:

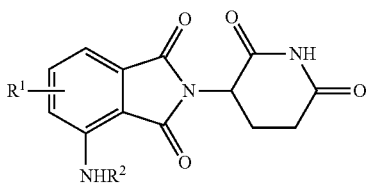

(II)

or an enantiomer or a mixture of enantiomers thereof; and (ii) deprotecting the compound of Formula II to form the compound of Formula I;

wherein $R^1$ is hydrogen, hydroxyl, or $-OR^{1a}$; and $R^{1a}$ is a hydroxyl protecting group.

Additionally provided herein is a process for preparing a compound of Formula I:

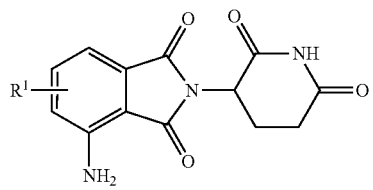

(I)

or an enantiomer or a mixture of enantiomers thereof; or a pharmaceutically acceptable salt, solvate, hydrate, or polymorph thereof;

comprising the step of reducing a compound of Formula III:

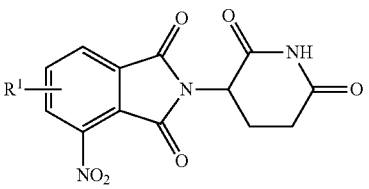

(III)

to form the compound of Formula I;

wherein $R^1$ is hydroxyl or $-OR^{1a}$; and $R^{1a}$ is a hydroxyl protecting group.

Furthermore, provided herein is a process for preparing a compound of Formula I:

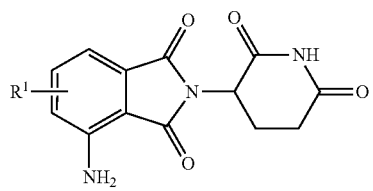

(I)

or an enantiomer or a mixture of enantiomers thereof; or a pharmaceutically acceptable salt, solvate, hydrate, or polymorph thereof;

comprising the step of converting the carboxyl group of a compound of Formula IV:

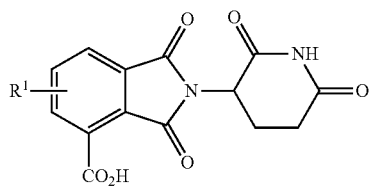

(IV)

to an amino group, thus to form the compound of Formula I; wherein $R^1$ is hydrogen, hydroxyl, or $-OR^{1a}$; and $R^{1a}$ is a hydroxyl protecting group.

V. DETAILED DESCRIPTION

Unless defined otherwise, all technical and scientific terms used herein have the same meaning as those commonly understood by one of ordinary skill in the art. All publications and patents referred to herein are incorporated by reference herein in their entireties.

A. Definitions

To facilitate understanding of the disclosure set forth herein, a number of terms are defined below. Generally, the nomenclature used herein and the laboratory procedures in organic chemistry described herein are those well known and commonly employed in the art.

The terms "process" and "method" are used interchangeably to refer to a method disclosed herein for a compound preparation. Modifications to the processes and methods disclosed herein (e.g., starting materials, reagents, protecting groups, solvents, temperatures, reaction times, and/or purification) that are well known to those of ordinary skill in the art are also encompassed by the disclosure.

The terms "adding," "reacting," and "mixing" are used interchangeably to refer to contacting one reactant, reagent, solvent, catalyst, or a reactive group with another reactant, reagent, solvent, catalyst, or reactive group. Unless otherwise specified, reactants, reagents, solvents, catalysts, and reactive groups can be added individually, simultaneously, or separately, and/or can be added in any order unless specified specifically. They can be added in the presence or absence of heat, and can optionally be added under an inert atmosphere (e.g., $N_2$ or Ar). In certain embodiments, the term "reacting" can also refer to in situ formation or intra-molecular reaction where the reactive groups are in the same molecule.

The term "protecting" or "protection" refers to contacting a functional group, such as an amino group, a hydroxyl group, and a carboxyl group, with a reagent to form a protecting group on that functional group.

The term "deprotecting" or "deprotection" refers to a process of restoring a functional group, such as an amino group, a hydroxyl group, and a carboxyl group, on a compound by removing a protecting group on that functional group.

The term "amino protecting group" refers to a protecting group suitable for preventing undesired reactions at an amino group. Examples of amino protecting groups include, but are not limited to, formyl, acetyl (Ac), trifluoroacetyl, nitrophenylacetyl, benzoyl (Bz), methoxycarbonyl, ethoxycarbonyl, tert-butoxycarbonyl (Boc), 1-methyl-1-(4-biphenylyl)-ethoxy-carbonyl (Bpoc), allyloxycarbonyl (Alloc), benzyloxycarbonyl (Cbz), p-methoxybenzylcarbonyl (Moz), 9-fluorenylmethoxycarbonyl (Fmoc), 2-trimethylsilylethoxycarbonyl (Teoc), tosyl (Ts), and nitrobenzenesulfonyl. Additional examples of amino protecting groups are described in *Greene's Protective Groups in Organic Synthesis,* 4th edition, John Wiley & Sons, New York, 2007.

The term "carboxyl protecting group" refers to a protecting group suitable for preventing undesired reactions at a carboxyl group. Examples of carboxyl protecting groups include, but are not limited to, methyl, 9-fluorenylmethyl, methoxymethyl, methylthiomethyl, tetrahydropyranyl, tetrahydrofuranyl, methoxyethoxymethyl, 2-(trimethylsilyl) ethoxymethyl, benzyloxymethyl, ethyl, 2,2,2-trichloroethyl, 2-(trimethylsilyl)ethyl, 2-methylthioethyl, t-butyl (tBu), cyclopentyl, cyclohexyl, allyl, cinnamyl, phenyl, benzyl (Bn), triphenylmethyl (trityl), diphenylmethyl, trimethylsilyl, triethylsilyl, t-butyldimethylsilyl, phenyldimethylsilyl, and di-t-butylmethylsilyl. Additional examples of carboxyl protecting groups are described in *Greene's Protective Groups in Organic Synthesis,* 4th edition, John Wiley & Sons, New York, 2007.

The term "hydroxyl protecting group" refers to a protecting group suitable for preventing undesired reactions at a hydroxyl group. Examples of hydroxyl protecting groups include, but are not limited to, allyl, methyl, 2-methoxyethoxymethyl (MEM), methoxymethyl (MOM), methoxythiomethyl, t-butoxymethyl, tri-isopropylsilyloxymethyl (TOM), ethyl, 1-ethoxyethyl, isopropyl, t-butyl, benzyl, trityl (Tr), dimethoxytrityl (DMT), monomethoxytrityl (MMT), p-methoxybenzyl (PMB), acetyl, chloroacetyl, trichloroacetyl, trifluoroacetyl, pivaloyl (Piv), benzoyl, p-phenylbenzoyl, trimethylsilyl (TMS), triisopropylsilyl (TIPS), t-butyldimethylsilyl (TBDMS), and tetrahydropyranyl. Additional examples of hydroxyl protecting groups are described in *Greene's Protective Groups in Organic Synthesis,* 4th edition, John Wiley & Sons, New York, 2007. In certain embodiments, the hydroxyl protecting group is a silyl group, including, but not limited to, trimethylsilyl, triisopropylsilyl, and t-butyldimethylsilyl.

The term "solvate" refers to a complex or aggregate formed by one or more molecules of a solute, e.g., an isoindoline-1, 3-dione compound, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "substantially complete" when referring to a reaction means that the reaction contains no greater than about 50%, no greater than about 40%, no greater than about 30%, no greater than about 20%, no greater than about 10%, no greater than about 5%, no greater than about 4%, no greater than about 3%, no greater than about 2%, no greater than about 1%, no greater than about 0.5%, no greater than about 0.1%, or no greater than about 0.05% of a starting material.

The term "substantially free" when referring to a composition that is "substantially free" of a compound means that the composition contains no greater than about 20% by weight, no greater than about 10% by weight, no greater than about 5% by weight, no greater than about 3% by weight, no greater than about 1% by weight, no greater than about 0.5% by weight, no greater than about 0.2% by weight, no greater than about 0.1% by weight, no greater than about 0.01% by weight, no greater than about 0.001% by weight, or no greater than about 0.0001% by weight of the compound.

The term "substantially pure" when referring to a compound or composition means that the compound or composition has a purity of no less than about 80% by weight, no less than about 90% by weight, no less than about 95% by weight, no less than about 96% by weight, no less than about 97% by weight, no less than about 98% by weight, no less than about 99% by weight, no less than about 99.5% by weight, no less than about 99.9% by weight, no less than about 99.95% by weight, no less than about 99.99% by weight, no less than about 99.995% by weight, no less than about 99.999% by weight, no less than about 99.9995% by weight, or no less than about 99.9999% by weight.

The phrase "an enantiomer or a mixture of enantiomers thereof; or a pharmaceutically acceptable salt, solvate, hydrate, or polymorph thereof" has the same meaning as the phrase "an enantiomer or a mixture of enantiomers of the compound referenced therein; a pharmaceutically acceptable salt, solvate, hydrate, or polymorph of the compound referenced therein; or a pharmaceutically acceptable salt, solvate, hydrate, or polymorph of an enantiomer or a mixture of enantiomers of the compound referenced therein."

The phrase "an enantiomer or a mixture of enantiomers thereof; or a salt thereof" has the same meaning as the phrase "an enantiomer or a mixture of enantiomers of the compound referenced therein; a salt of the compound referenced therein; or a salt of an enantiomer or a mixture of enantiomers of the compound referenced therein."

If the stereochemistry of a structure or a portion thereof is not indicated, e.g., with bold or dashed lines, the structure or portion thereof is to be interpreted as encompassing all stereoisomers of the structure.

B. Synthetic Processes

In one embodiment, provided herein is a process for preparing an isoindoline-1,3-dione compound of Formula I:

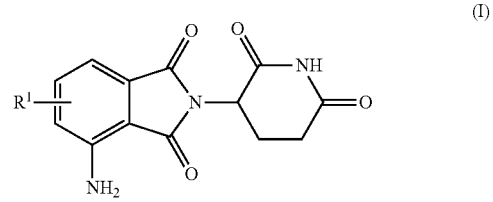

or an enantiomer or a mixture of enantiomers thereof; or a pharmaceutically acceptable salt, solvate, hydrate, or polymorph thereof;

comprising the step of reacting a compound of Formula Ia:

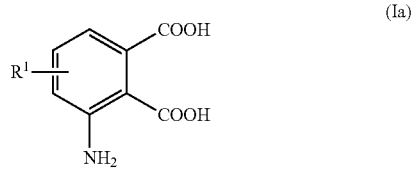

with 3-aminopiperidine-2,6-dione, or an enantiomer or a mixture of enantiomers thereof; or a salt thereof; to form the compound of Formula I;
wherein $R^1$ is hydrogen, hydroxyl, or —$OR^{1a}$; and $R^{1a}$ is a hydroxyl protecting group.

In certain embodiments, the 3-aminopiperidine-2,6-dione compound used in the process provided herein comprises 3-aminopiperidine-2,6-dione free base. In certain embodiments, the 3-aminopiperidine-2,6-dione compound used in the synthetic process provided herein is 3-aminopiperidine-2,6-dione free base. In certain embodiments, 3-aminopiperidine-2,6-dione free base is formed by neutralizing (i) a 3-aminopiperidine-2,6-dione salt, in one embodiment, 3-aminopiperidine-2,6-dione hydrochloride, with (ii) a base, in one embodiment, an organic base, in another embodiment, triethylamine. In certain embodiments, 3-aminopiperidine-2,6-dione free base is formed in situ by neutralizing (i) a 3-aminopiperidine-2,6-dione salt, in one embodiment, 3-aminopiperidine-2,6-dione hydrochloride, with (ii) a base, in one embodiment, an organic base, in another embodiment, triethylamine. In certain embodiments, the 3-aminopiperidine-2,6-dione salt is 3-aminopiperidine-2,6-dione hydrochloride. In certain embodiments, the base is an inorganic base. In certain embodiments, the base is an organic base, in one embodiment, an amine. In certain embodiments, the base is triethylamine or pyridine. In certain embodiments, the base is triethylamine. In certain embodiments, the base is pyridine.

In certain embodiments, the 3-aminopiperidine-2,6-dione compound used in the synthetic process provided herein comprises a 3-aminopiperidine-2,6-dione salt. In certain embodiments, the 3-aminopiperidine-2,6-dione compound used in the synthetic process provided herein is a 3-aminopiperidine-2,6-dione salt. In certain embodiments, the 3-aminopiperidine-2,6-dione salt is an organic salt of 3-aminopiperidine-2,6-dione. In certain embodiments, the 3-aminopiperidine-2,6-dione salt is an acetic acid salt of 3-aminopiperidine-2,6-dione. In certain embodiments, the 3-aminopiperidine-2,6-dione salt is an inorganic salt of 3-aminopiperidine-2,6-dione. In certain embodiments, the 3-aminopiperidine-2,6-dione salt is 3-aminopiperidine-2,6-dione hydrochloride.

In certain embodiments, the reaction of a compound of Formula Ia with a 3-aminopiperidine-2,6-dione compound is performed in the presence of a coupling reagent. Suitable coupling reagents include, but are not limited to, a carbodiimide, N-(3-dimethylaminopropyl)-N'-ethylcarbodiimide (EDC or EDCI), N-(3-dimethylaminopropyl)-N'-ethylcarbodiimide hydrochloride (EDC hydrochloride), 1-(3-dimethylaminopropyl)-3-ethylcarbodiimide methiodide (EDC methiodide), 1-cyclohexyl-3-(2-morpholinoethyl)carbodiimide metho-p-toluenesulfonate, 1,3-dicyclohexylcarbodiimide (DCC), 1,1'-carbonyldiimidazole (CDI), bis(2-oxo-3-oxazolidinyl)phosphinic chloride (BOP-Cl), O-(7-azabenzotriazol-1-yl)-N,N,N',N'-tetramethyluronium hexafluorophosphate (HATU), (7-azabenzotriazol-1-yloxy) tripyrrolidinophosphonium hexafluorophosphate (PyAOP), (benzotriazol-1-yloxy)tripyrrolidinophosphonium hexafluorophosphate (PyBOP), (benzotriazol-1-yloxy)tris(dimethylamino)phosphonium hexafluorophosphate (BOP reagent), N,N,N',N'-tetramethyl-O-(1H-benzotriazol-1-yl)uronium hexafluorophosphate (HBTU), O-(benzotriazol-1-yl)-N,N,N',N'-tetramethyluronium tetrafluoroborate (TBTU), O-(benzotriazol-1-yl)-N,N,N',N'-bis(tetramethylene)uronium hexafluorophosphate (HBPyU), O-(benzotriazol-1-yl)-N,N,N',N'-bis(pentamethylene)uronium hexafluorophosphate, acetic anhydride, $SOCl_2$, $PCl_3$, $POCl_3$, $PCl_5$, and mixtures thereof. In certain embodiments, the coupling reagent is a carbodiimide. In certain embodiments, the coupling reagent is CDI. In certain embodiments, the coupling reagent is EDCI.

In certain embodiments, the reaction of a compound of Formula Ia with a 3-aminopiperidine-2,6-dione compound is performed in the presence of a base. In certain embodiments, the base is an inorganic base. In certain embodiments, the base is an organic base. In certain embodiments, the base is triethylamine or pyridine. In certain embodiments, the base is triethylamine. In certain embodiments, the base is pyridine.

In certain embodiments, the reaction of a compound of Formula Ia with a 3-aminopiperidine-2,6-dione compound is performed in a solvent. Suitable solvents include, but are not limited to, petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl) ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methylpyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water, and mixtures thereof. In certain embodiments, the solvent is an inorganic solvent. In certain embodiments, the solvent is an organic solvent. In certain embodiments, the solvent is an acid. In certain embodiments, the solvent is an organic acid. In certain embodiments, the solvent is acetic acid.

In certain embodiments, the reaction of a compound of Formula Ia with a 3-aminopiperidine-2,6-dione compound is performed at an elevated temperature. In certain embodiments, the reaction temperature is ranging from about 30 to about 200° C., from about 50 to about 150° C., or from about 100 to about 150° C. In certain embodiments, the reaction temperature is about 90, about 100, about 110, about 120, about 130, about 140, or about 150° C. In certain embodiments, the reaction temperature is about 110, about 120, or about 130° C. In certain embodiments, the reaction temperature is about 120° C.

In certain embodiments, $R^1$ is hydrogen. In certain embodiments, $R^1$ is hydroxyl. In certain embodiments, $R^1$ is —$OR^{1a}$, wherein $R^{1a}$ is a hydroxyl protecting group. In certain embodiments, $R^{1a}$ is $C_{1-6}$ alkyl. In certain embodiments, $R^{1a}$ is methyl, ethyl, propyl, t-butyl, or benzyl. In certain embodiments, $R^{1a}$ is methyl or isopropyl. In certain embodiments, $R^{1a}$ is methyl. In certain embodiments, $R^{1a}$ is isopropyl. In certain embodiments, $R^1$ is hydrogen, hydroxyl, methoxy, ethoxy, isopropoxy, t-butoxy, or benzyloxy. In certain embodiments, $R^1$ is hydrogen, hydroxyl, methoxy, or isopropoxy. In certain embodiments, $R^1$ is hydroxyl, methoxy, or isopropoxy. In certain embodiments, $R^1$ is hydroxyl. In certain embodiments, $R^1$ is methoxy. In certain embodiments, $R^1$ is isopropoxy.

In certain embodiments, the compound of Formula Ia is 3-amino-phthalic acid, 3-amino-4-hydroxy-phthalic acid, 3-amino-5-hydroxy-phthalic acid, or 3-amino-6-hydroxy-phthalic acid. In certain embodiments, the compound of Formula Ia is 3-amino-4-hydroxy-phthalic acid, 3-amino-5-hydroxy-phthalic acid, or 3-amino-6-hydroxy-phthalic acid. In certain embodiments, the compound of Formula Ia is 3-amino-phthalic acid. In certain embodiments, the compound of Formula Ia is 3-amino-4-hydroxy-phthalic acid. In certain embodiments, the compound of Formula Ia is 3-amino-5-hydroxy-phthalic acid. In certain embodiments, the compound of Formula Ia is 3-amino-6-hydroxy-phthalic acid.

In certain embodiments, the compound of Formula I is 4-amino-2-(2,6-dioxo-piperidin-3-yl)-isoindole-1,3-dione, 4-amino-2-(2,6-dioxo-piperidin-3-yl)-5-hydroxy-isoindole-1,3-dione, 4-amino-2-(2,6-dioxo-piperidin-3-yl)-6-hydroxy-isoindole-1,3-dione, or 4-amino-2-(2,6-dioxo-piperidin-3-yl)-7-hydroxy-isoindole-1,3-dione; or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-5-hydroxy-isoindole-1,3-dione, 4-amino-2-(2,6-dioxo-piperidin-3-yl)-6-hydroxy-isoindole-1,3-dione, or 4-amino-2-(2,6-dioxo-piperidin-3-yl)-7-hydroxy-isoindole-1,3-dione; or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-5-hydroxy-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-6-hydroxy-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-7-hydroxy-isoindole-1,3-dione, or an enantiomer or a mixture of enantiomers thereof; or a pharmaceutically acceptable salt, solvate, hydrate, or polymorph thereof.

In certain embodiments, when $R^1$ is a protected hydroxyl, the process provided herein further comprises a step of removing the hydroxyl protecting group to form hydroxyl. In certain embodiments, the deprotection is performed with an acid. In certain embodiments, the acid is a Lewis acid. In certain embodiments, the acid is $AlCl_3$, $AlBr_3$, $BCl_3$, or $BBr_3$. In certain embodiments, the acid is $BCl_3$ or $BBr_3$.

In one embodiment, the process provided herein is for preparing an isoindoline-1,3-dione compound of Formula I, or an enantiomer or a mixture of enantiomers thereof; or a pharmaceutically acceptable salt, solvate, hydrate, or polymorph thereof; comprises the step of reacting a compound of Formula Ia with (i) a 3-aminopiperidine-2,6-dione salt, in one embodiment, 3-aminopiperidine-2,6-dione hydrochloride, or an enantiomer or a mixture of enantiomers thereof; in the presence of (ii) a base, in one embodiment, an organic base, in another embodiment, triethylamine; in (iii) a solvent, in one embodiment, an organic acid, in another embodiment, acetic acid; at (iv) an elevated temperature, in one embodiment, about 120° C.; to form the compound of Formula I.

In another embodiment, the process provided herein is for preparing 4-amino-2-(2,6-dioxopiperidin-3-yl)-5-hydroxy-isoindoline-1,3-dione:

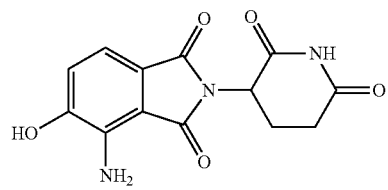 [SMILES: Nc1c(O)ccc2c1C(=O)N(C1CCC(=O)NC1=O)C2=O]

or an enantiomer or a mixture of enantiomers thereof; or a pharmaceutically acceptable salt, solvate, hydrate, or polymorph thereof;

comprising the step of reacting 3-amino-4-hydroxyphthalic acid:

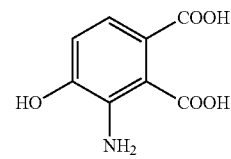 [SMILES: Nc1c(O)ccc(C(=O)O)c1C(=O)O]

with a 3-aminopiperidine-2,6-dione salt, in one embodiment, 3-aminopiperidine-2,6-dione salt hydrochloride, or an enantiomer or a mixture of enantiomers thereof; to form 4-amino-2-(2,6-dioxopiperidin-3-yl)-5-hydroxyisoindoline-1,3-dione.

In yet another embodiment, the process for preparing 4-amino-2-(2,6-dioxopiperidin-3-yl)-5-hydroxyisoindoline-1,3-dione, or an enantiomer or a mixture of enantiomers thereof; or a pharmaceutically acceptable salt, solvate, hydrate, or polymorph thereof; comprises the step of reacting 3-amino-4-hydroxyphthalic acid with 3-aminopiperidine-2,6-dione hydrochloride, or an enantiomer or a mixture of enantiomers thereof; in the presence of (i) a base, in one embodiment, an organic base, in another embodiment, triethylamine; in (ii) a solvent, in one embodiment, an organic acid, in another embodiment, acetic acid; at (iii) an elevated temperature, in one embodiment, 120° C.; to form 4-amino-2-(2,6-dioxopiperidin-3-yl)-5-hydroxyisoindoline-1,3-dione.

In one embodiment, the process for preparing 4-amino-2-(2,6-dioxopiperidin-3-yl)-5-hydroxyisoindoline-1,3-dione further comprises a process for preparing 3-amino-4-hydroxyphthalic acid, which comprises the step of hydrolyzing dimethyl 3-amino-4-hydroxyphthalate to form 3-amino-4-hydroxyphthalic acid; wherein the methyl groups each function as a carboxyl protecting group. Thus, other suitable carboxyl protecting groups can also be employed in the place of the methyl groups. In certain embodiments, the carboxyl protecting groups are each independently methyl, ethyl, tert-butyl, phenyl, or benzyl. In certain embodiments, the carboxyl protecting groups are each independently methyl, ethyl, phenyl, or benzyl. In certain embodiments, the carboxyl protecting groups are methyl.

In certain embodiments, the hydrolysis is performed in the presence of a base. In certain embodiments, the base is an inorganic base. In certain embodiments, the base is sodium hydroxide, potassium hydroxide, lithium hydroxide, sodium carbonate, potassium carbonate, or cesium carbonate. In certain embodiments, the base is sodium hydroxide. In certain embodiments, the base is an organic base. In certain embodiments, the base is triethylamine.

In certain embodiments, the hydrolysis is performed in the presence of an acid. In certain embodiments, the acid is an organic acid. In certain embodiments, the acid is an inorganic acid. In certain embodiments, the acid is hydrochloric acid or sulfuric acid. In certain embodiments, the acid is hydrochloric acid.

In certain embodiments, the hydrolysis is performed in the presence of a solvent. In certain embodiments, the solvent comprises an inorganic solvent. In certain embodiments, the solvent comprises an organic solvent. In certain embodiments, the solvent comprises an organic solvent and an inorganic solvent. In certain embodiments, the solvent comprises water. In certain embodiments, the solvent comprises ethanol. In certain embodiments, the solvent comprises water and ethanol. In certain embodiments, the solvent is a mixture of water and ethanol.

In certain embodiments, the hydrolysis is performed at an elevated temperature. In certain embodiments, the temperature is ranging from about 30 to about 150° C., from about 40 to about 125° C., or from about 50 to about 100° C. In certain embodiments, the temperature is about 50, about 60, about 70, about 80, or about 90° C. In certain embodiments, the temperature is about 70° C.

In another embodiment, the process for preparing 4-amino-2-(2,6-dioxopiperidin-3-yl)-5-hydroxyisoindoline-1,3-dione further comprises a process for preparing dimethyl 3-amino-4-hydroxyphthalate, which comprises reducing dimethyl 4-hydroxy-3-nitrophthalate to form dimethyl 3-amino-4-hydroxyphthalate; wherein the methyl groups each function as a carboxyl protecting group. Thus, other suitable carboxyl protecting groups can also be employed in the place of the methyl groups. In certain embodiments, the carboxyl protecting groups are each independently methyl, ethyl, tert-butyl, phenyl, or benzyl. In certain embodiments, the carboxyl protecting groups are each independently methyl, ethyl, phenyl, or benzyl. In certain embodiments, the carboxyl protecting groups are methyl.

In certain embodiments, the reduction is performed via catalytic hydrogenation in the presence of a catalyst. In certain embodiments, the catalyst is a heterogeneous hydrogenation catalyst. In certain embodiments, the catalyst is Raney nickel, palladium, palladium black, palladium on carbon (Pd/C), palladium oxide, Lindlar catalyst, platinum, platinum black, platinum on carbon (Pt/C), or platinum dioxide (Adam's catalyst). In certain embodiments, the catalyst is a homogeneous hydrogenation catalyst. In certain embodiments, the homogeneous catalyst is an iridium-based catalyst. In certain embodiments, the homogeneous catalyst is a palladium-based catalyst. In certain embodiments, the homogeneous catalyst is a platinum-based catalyst. In certain embodiments, the homogeneous catalyst is a rhodium-based catalyst. In certain embodiments, the homogeneous catalyst is chloro-tris(triphenylphosphine)rhodium(I) (Wilkinson's catalyst). In certain embodiments, the homogeneous catalyst is an iridium-based catalyst. In certain embodiments, the homogeneous catalyst is Crabtree's catalyst.

In certain embodiments, the catalyst is a precious metal catalyst. In certain embodiments, the catalyst is an iridium, palladium, platinum, rhodium, or ruthenium catalyst. In certain embodiments, the catalyst is an iridium catalyst. In certain embodiments, the catalyst is a palladium catalyst. In certain embodiments, the catalyst is palladium, palladium black, palladium on carbon (Pd/C), palladium oxide, or Lindlar catalyst. In certain embodiments, the catalyst is palladium. In certain embodiments, the catalyst is palladium black. In certain embodiments, the catalyst is palladium on carbon (Pd/C). In certain embodiments, the catalyst is palladium oxide. In certain embodiments, the catalyst is Lindlar catalyst. In certain embodiments, the catalyst is a platinum catalyst. In certain embodiments, the catalyst is platinum, platinum black, platinum on carbon (Pt/C), or platinum dioxide ($PtO_2$). In certain embodiments, the catalyst is platinum. In certain embodiments, the catalyst is platinum black. In certain embodiments, the catalyst is platinum on carbon (Pt/C). In certain embodiments, the catalyst is platinum dioxide. In certain embodiments, the catalyst is a rhodium catalyst. In certain embodiments, the catalyst is a ruthenium catalyst.

In certain embodiments, the catalyst is a non-precious metal catalyst. In certain embodiments, the catalyst is a nickel catalyst. In certain embodiments, the catalyst is Raney nickel.

In certain embodiments, the reduction is performed using a reducing agent. In certain embodiments, the reducing agent comprises iron and an acid. In certain embodiments, the reducing agent is Fe/HCl. In certain embodiments, the reducing agent comprises zinc and an acid. In certain embodiments, the reducing agent is Zn/HOAc. In certain embodiments, the reducing agent is samarium diiodide. In certain embodiments, the reducing agent is hydrogen ($H_2$), formic acid, ammonium formate, hypophosphorous acid, cyclohexene, cyclohexadiene, diimide, or carbon monooxide.

In certain embodiments, the reduction is performed in the presence of a solvent. In certain embodiments, the solvent is methanol.

In certain embodiments, the reduction is performed at a temperature ranging from about 0 to about 150° C., from about 10 to about 100° C., or from about 15 to about 50° C. In certain embodiments, the temperature is about 10, about 20, about 30, about 40, or about 50° C. In certain embodiments, the temperature is about 25° C. In certain embodiments, the temperature is room temperature.

In yet another embodiment, the process for preparing 4-amino-2-(2,6-dioxopiperidin-3-yl)-5-hydroxyisoindoline-1,3-dione further comprises a process for preparing dimethyl 4-hydroxy-3-nitrophthalate, which comprises the step of reacting dimethyl 4-hydroxyphthalate with a nitration reagent to form dimethyl 4-hydroxy-3-nitrophthalate; wherein the methyl groups are each functioning as a carboxyl protecting group. Thus, other suitable carboxyl protecting groups can also be employed in the place of the methyl groups. In certain embodiments, the carboxyl protecting groups are each independently methyl, ethyl, tert-butyl, phenyl, or benzyl. In certain embodiments, the carboxyl protecting groups are each independently methyl, ethyl, phenyl, or benzyl. In certain embodiments, the carboxyl protecting groups are methyl.

In certain embodiments, the nitration reagent comprises nitric acid. In certain embodiments, the nitration reagent comprises nitric acid and sulfuric acid. In certain embodiments, the nitration reagent is a mixture of nitric acid and sulfuric acid.

In certain embodiments, the nitration is performed at a temperature ranging from about 0 to about 150° C., from about 10 to about 100° C., or from about 15 to about 50° C. In certain embodiments, the temperature is about 10, about 15, about 20, about 25, about 30, about 35, or about 40° C. In certain embodiments, the temperature is about 25° C. In certain embodiments, the temperature is room temperature.

In yet another embodiment, the process for preparing 4-amino-2-(2,6-dioxopiperidin-3-yl)-5-hydroxyisoindoline-1,3-dione further comprises a process for preparing dimethyl 4-hydroxyphthalate, which comprises the step of reacting 4-hydroxyphthalic acid with methanol to form dimethyl 4-hydroxyphthalate; wherein the methyl groups are each functioning as a carboxyl protecting group. Thus, other suitable carboxyl protecting groups can also be employed in the place of the methyl groups. In certain embodiments, the carboxyl protecting groups are each independently methyl, ethyl, tert-butyl, phenyl, or benzyl. In certain embodiments, the carboxyl protecting groups are each independently methyl, ethyl, phenyl, or benzyl. In certain embodiments, the carboxyl protecting groups are methyl.

In certain embodiments, the carboxyl protection is performed in the presence of a coupling reagent. In certain embodiments, the coupling reagent is $SOCl_2$, $POCl_3$, or EDCI. In certain embodiments, the coupling reagent is $SOCl_2$.

In certain embodiments, the carboxyl protection is performed via an esterification reaction. In certain embodiments, the carboxyl protection is performed in the presence of an acid. In certain embodiments, the carboxyl protection is performed via the Fisher esterification.

In certain embodiments, the carboxyl protection is performed in the presence of a solvent. In certain embodiments, the solvent is methanol, ethanol, phenol, or benzyl alcohol, to form methyl, ethyl, phenyl, or benzyl protecting group, respectively. In certain embodiments, the solvent is methanol.

In certain embodiments, the carboxyl protection is performed at an elevated temperature. In certain embodiments, the temperature is ranging from about 30 to about 150° C., from about 40 to about 125° C., or from about 50 to about 100° C. In certain embodiments, the temperature is about 60, about 70, about 80, about 90, about 100, or about 110° C. In certain embodiments, the temperature is about 80° C.

In yet another embodiment, the process provided herein for preparing 4-amino-2-(2,6-dioxopiperidin-3-yl)-5-hydroxyisoindoline-1,3-dione, or an enantiomer or a mixture of enantiomers thereof; or a pharmaceutically acceptable salt, solvate, hydrate, or polymorph thereof; comprises the steps of:
(i) protecting 4-hydroxyphthalic acid to form a carboxyl protected 4-hydroxyphthalic acid;
(ii) reacting the carboxyl protected 4-hydroxyphthalic acid with a nitration reagent, in one embodiment, nitric acid/sulfuric acid, to form a carboxyl protected 4-hydroxy-3-nitrophthalic acid;
(iii) reducing the carboxyl protected 4-hydroxy-3-nitrophthalic acid, in one embodiment, via catalytic hydrogenation, to form a carboxyl protected 3-amino-4-hydroxyphthalic acid;
(iv) deprotecting the carboxyl protected 3-amino-4-hydroxyphthalic acid, in one embodiment, with a base, in another embodiment, with sodium hydroxide, to form 3-amino-4-hydroxyphthalic acid; and
(v) reacting 3-amino-4-hydroxyphthalic acid with 3-aminopiperidine-2,6-dione hydrochloride, or an enantiomer or a mixture of enantiomers thereof; to form 4-amino-2-(2,6-dioxopiperidin-3-yl)-5-hydroxyisoindoline-1,3-dione.

In still another embodiment, the process provided herein for preparing 4-amino-2-(2,6-dioxopiperidin-3-yl)-5-hydroxyisoindoline-1,3-dione, or an enantiomer or a mixture of enantiomers thereof; or a pharmaceutically acceptable salt, solvate, hydrate, or polymorph thereof; comprises the steps of:
(i) reacting 4-hydroxyphthalic acid with methanol in the presence of a coupling reagent, in one embodiment, a coupling reagent, in another embodiment, $SOCl_2$, to form dimethyl 4-hydroxyphthalate;
(ii) reacting dimethyl 4-hydroxyphthalate with a nitration reagent, in one embodiment, nitric acid/sulfuric acid, to form dimethyl 4-hydroxy-3-nitrophthalate;
(iii) reducing dimethyl 4-hydroxy-3-nitrophthalate, in one embodiment, via catalytic hydrogenation, to form dimethyl 3-amino-4-hydroxyphthalate;
(iv) hydrolyzing dimethyl 3-amino-4-hydroxyphthalate, in one embodiment, with sodium hydroxide, to form 3-amino-4-hydroxyphthalic acid; and
(v) reacting 3-amino-4-hydroxyphthalic acid with 3-aminopiperidine-2,6-dione hydrochloride, or an enantiomer or a mixture of enantiomers thereof; to form 4-amino-2-(2,6-dioxopiperidin-3-yl)-5-hydroxyisoindoline-1,3-dione.

In another embodiment, provided herein is a process for preparing an isoindoline-1,3-dione compound of Formula I:

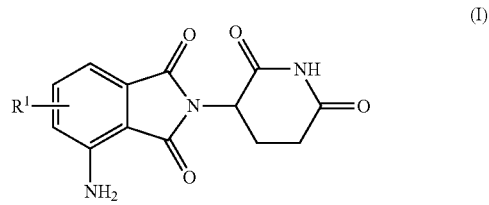

or an enantiomer or a mixture of enantiomers thereof; or a pharmaceutically acceptable salt, solvate, hydrate, or polymorph thereof;
comprising the steps of:
(i) reacting a compound of Formula IIa:

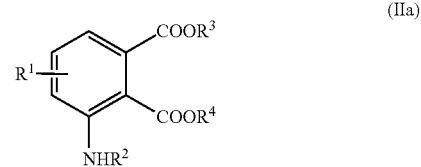

wherein:
$R^2$ is an amino protecting group; and
$R^3$ and $R^4$ are each independently hydrogen or a carboxyl protecting group; with 3-aminopiperidine-2,6-dione, or an enantiomer or a mixture of enantiomers thereof; or a salt thereof; to form a compound of Formula II:

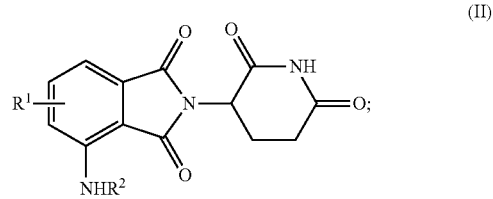

and (ii) deprotecting the compound of Formula II to form the compound of Formula I;
wherein $R^1$ is hydrogen, hydroxyl, or —$OR^{1a}$; and $R^{1a}$ is a hydroxyl protecting group.

In certain embodiments, the 3-aminopiperidine-2,6-dione compound used in the process provided herein comprises 3-aminopiperidine-2,6-dione free base. In certain embodiments, the 3-aminopiperidine-2,6-dione compound used in the synthetic process provided herein is 3-aminopiperidine-2,6-dione free base. In certain embodiments, 3-aminopiperidine-2,6-dione free base is formed by neutralizing (i) a 3-aminopiperidine-2,6-dione salt, in one embodiment, 3-aminopiperidine-2,6-dione hydrochloride, with (ii) a base, in one embodiment, an organic base, in another embodiment, triethylamine. In certain embodiments, 3-aminopiperidine-2,6-dione free base is formed in situ by neutralizing (i) a 3-aminopiperidine-2,6-dione salt, in one embodiment, 3-aminopiperidine-2,6-dione hydrochloride, with (ii) a base, in one embodiment, an organic base, in another embodiment, triethylamine. In certain embodiments, the 3-aminopiperidine-2,6-dione salt is 3-aminopiperidine-2,6-dione hydrochloride. In certain embodiments, the base is an inorganic base. In certain embodiments, the base is an organic base, in one embodiment, an amine. In certain embodiments, the base is triethylamine or pyridine. In certain embodiments, the base is triethylamine. In certain embodiments, the base is pyridine.

In certain embodiments, the 3-aminopiperidine-2,6-dione compound used in the synthetic process provided herein comprises a 3-aminopiperidine-2,6-dione salt. In certain embodiments, the 3-aminopiperidine-2,6-dione compound used in the synthetic process provided herein is a 3-aminopiperidine-2,6-dione salt. In certain embodiments, the 3-aminopiperidine-2,6-dione salt is an organic salt of 3-aminopiperidine-2,6-dione. In certain embodiments, the 3-aminopiperidine-2,6-dione salt is an acetic acid salt of 3-aminopiperidine-2,6-dione. In certain embodiments, the 3-aminopiperidine-2,6-dione salt is an inorganic salt of 3-aminopiperidine-2,6-dione. In certain embodiments, the 3-aminopiperidine-2,6-dione salt is 3-aminopiperidine-2,6-dione hydrochloride.

In certain embodiments, the reaction of a compound of Formula IIa with a 3-aminopiperidine-2,6-dione compound is performed in the presence of a coupling reagent.

In certain embodiments, the reaction of a compound of Formula IIa with a 3-aminopiperidine-2,6-dione compound is performed in the presence of a base. In certain embodiments, the base is an inorganic base. In certain embodiments, the base is an organic base. In certain embodiments, the base is triethylamine or pyridine. In certain embodiments, the base is pyridine.

In certain embodiments, the reaction of a compound of Formula IIa with a 3-aminopiperidine-2,6-dione compound is performed in a solvent. In certain embodiments, the solvent is an organic solvent. In certain embodiments, the solvent is pyridine.

In certain embodiments, the reaction of a compound of Formula IIa with a 3-aminopiperidine-2,6-dione compound is performed at an elevated temperature. In certain embodiments, the reaction temperature is ranging from about 30 to about 150° C., from about 50 to about 150° C., or from about 75 to about 125° C. In certain embodiments, the reaction temperature is about 70, about 80, about 90, about 100, about 110, about 120, or about 130° C. In certain embodiments, the reaction temperature is about 90, about 100, or about 110° C. In certain embodiments, the reaction temperature is about 100° C.

In certain embodiments, the deprotection of a compound of Formula II is performed in the presence of a deprotecting reagent for an amino protecting group. In certain embodiments, the deprotecting reagent is for removing a Boc group. In certain embodiments, the deprotecting reagent is an acid. In certain embodiments, the deprotecting reagent is an organic acid. In certain embodiments, the deprotecting reagent is trifluoroacetic acid. In certain embodiments, the deprotecting reagent is an inorganic acid. In certain embodiments, the deprotecting reagent is hydrochloric acid.

In certain embodiments, the deprotection is performed in the presence of a solvent. In certain embodiments, the solvent is an inorganic solvent. In certain embodiments, the solvent is an organic solvent. In certain embodiments, the solvent is dichloromethane (DCM).

In certain embodiments, the deprotection is performed at a temperature ranging from about 0 to about 150° C., from about 10 to about 100° C., or from about 15 to about 50° C. In certain embodiments, the temperature is about 10, about 15, about 20, about 25, about 30, about 35, or about 40° C. In certain embodiments, the temperature is about 25° C. In certain embodiments, the temperature is room temperature.

In certain embodiments, $R^1$ is hydrogen. In certain embodiments, $R^1$ is hydroxyl. In certain embodiments, $R^1$ is —$OR^{1a}$, wherein $R^{1a}$ is a hydroxyl protecting group. In certain embodiments, $R^{1a}$ is $C_{1-6}$ alkyl. In certain embodiments, $R^{1a}$ is methyl, ethyl, propyl, t-butyl, or benzyl. In certain embodiments, $R^{1a}$ is methyl or isopropyl. In certain embodiments, $R^{1a}$ is methyl. In certain embodiments, $R^{1a}$ is isopropyl. In certain embodiments, $R^1$ is hydrogen, hydroxyl, methoxy, ethoxy, isopropoxy, or benzyl. In certain embodiments, $R^1$ is hydrogen, hydroxyl, methoxy, or isopropoxy. In certain embodiments, $R^1$ is hydroxyl, methoxy, or isopropoxy. In certain embodiments, $R^1$ is hydroxyl. In certain embodiments, $R^1$ is methoxy. In certain embodiments, $R^1$ is isopropoxy.

In certain embodiments, $R^2$ is an amino protecting group. In certain embodiments, $R^2$ is Boc, Cbz, or Fmoc. In certain embodiments, $R^2$ is Boc. In certain embodiments, $R^2$ is Cbz. In certain embodiments, $R^2$ is Fmoc.

In certain embodiments, $R^3$ is hydrogen. In certain embodiments, $R^3$ is a carboxyl protecting group. In certain embodiments, $R^3$ is methyl, ethyl, phenyl, or benzyl. In certain embodiments, $R^3$ is methyl. In certain embodiments, $R^3$ is ethyl. In certain embodiments, $R^3$ is phenyl. In certain embodiments, $R^3$ is benzyl.

In certain embodiments, $R^4$ is hydrogen. In certain embodiments, $R^4$ is a carboxyl protecting group. In certain embodiments, $R^4$ is methyl, ethyl, phenyl, or benzyl. In certain embodiments, $R^4$ is methyl. In certain embodiments, $R^4$ is ethyl. In certain embodiments, $R^4$ is phenyl. In certain embodiments, $R^4$ is benzyl.

In certain embodiments, $R^3$ and $R^4$ are different. In certain embodiments, $R^3$ and $R^4$ are methyl, ethyl, phenyl, or benzyl. In certain embodiments, $R^3$ and $R^4$ are the same. In certain embodiments, $R^3$ and $R^4$ are both hydrogen. In certain embodiments, $R^3$ and $R^4$ are the same and both methyl, ethyl, phenyl, or benzyl. In certain embodiments, $R^3$ and $R^4$ are both methyl. In certain embodiments, $R^3$ and $R^4$ are both ethyl. In certain embodiments, $R^3$ and $R^4$ are both phenyl. In certain embodiments, $R^3$ and $R^4$ are both benzyl.

In certain embodiments, the compound of Formula IIa is 3-tert-butoxycarbonylaminophthalic acid dimethyl ester, 3-tert-butoxycarbonylamino-4-hydroxy-phthalic acid dimethyl ester, 3-tert-butoxycarbonylamino-5-hydroxy-phthalic acid dimethyl ester, or 3-tert-butoxycarbonylamino-6-hydroxy-phthalic acid dimethyl ester. In certain embodiments, the compound of Formula IIa is 3-tert-butoxycarbonylamino-4-hydroxy-phthalic acid dimethyl ester, 3-tert-butoxycarbonylamino-5-hydroxy-phthalic acid dimethyl ester, or 3-tert-butoxycarbonylamino-6-hydroxy-phthalic acid dimethyl ester. In certain embodiments, the compound of Formula IIa is 3-tert-butoxycarbonylaminophthalic acid dimethyl ester. In certain embodiments, the compound of Formula IIa is 3-tert-butoxycarbonylamino-4-hydroxy-phthalic acid dimethyl ester. In certain embodiments, the compound of Formula IIa is 3-tert-butoxycarbonylamino-5-hydroxy-phthalic acid dimethyl ester. In certain embodiments, the compound of Formula IIa is 3-tert-butoxycarbonylamino-6-hydroxy-phthalic acid dimethyl ester.

In certain embodiments, the compound of Formula II is (2-(2,6-dioxo-piperidin-3-yl)-1,3-dioxo-2,3-dihydro-1H-isoindol-4-yl)-carbamic acid tert-butyl ester, (2-(2,6-dioxo-piperidin-3-yl)-5-hydroxy-1,3-dioxo-2,3-dihydro-1H-isoindol-4-yl)-carbamic acid tert-butyl ester, (2-(2,6-dioxo-piperidin-3-yl)-6-hydroxy-1,3-dioxo-2,3-dihydro-1H-isoindol-4-yl)-carbamic acid tert-butyl ester, or (2-(2,6-dioxo-piperidin-3-yl)-7-hydroxy-1,3-dioxo-2,3-dihydro-1H-isoindol-4-yl)-carbamic acid tert-butyl ester; or an enantiomer or a mixture of enantiomers thereof. In certain embodiments, the compound of Formula II is (2-(2,6-dioxo-piperidin-3-yl)-5-hydroxy-1,3-dioxo-2,3-dihydro-1H-isoindol-4-yl)-carbamic acid tert-butyl ester, (2-(2,6-dioxo-piperidin-3-yl)-6-hydroxy-1,3-dioxo-2,3-dihydro-1H-isoindol-4-yl)-carbamic acid tert-butyl ester, or (2-(2,6-dioxo-piperidin-3-yl)-7-hydroxy-1,3-dioxo-2,3-dihydro-1H-isoindol-4-yl)-carbamic acid tert-butyl ester; or an enantiomer or a mixture of enantiomers thereof. In certain embodiments, the compound of Formula II is (2-(2,6-dioxo-piperidin-3-yl)-1,3-dioxo-2,3-dihydro-1H-isoindol-4-yl)-carbamic acid tert-butyl ester, or an enantiomer or a mixture of enantiomers thereof. In certain embodiments, the compound of Formula II is (2-(2,6-dioxo-piperidin-3-yl)-5-hydroxy-1,3-dioxo-2,3-dihydro-1H-isoindol-4-yl)-carbamic acid tert-butyl ester, or an enantiomer or a mixture of enantiomers thereof. In certain embodiments, the compound of Formula II is (2-(2,6-dioxo-piperidin-3-yl)-6-hydroxy-1,3-dioxo-2,3-dihydro-1H-isoindol-4-yl)-carbamic acid tert-butyl ester, or an enantiomer or a mixture of enantiomers thereof. In certain embodiments, the compound of Formula II is (2-(2,6-dioxo-piperidin-3-yl)-7-hydroxy-1,3-dioxo-2,3-dihydro-1H-isoindol-4-yl)-carbamic acid tert-butyl ester, or an enantiomer or a mixture of enantiomers thereof.

In certain embodiments, the compound of Formula I is 4-amino-2-(2,6-dioxo-piperidin-3-yl)-isoindole-1,3-dione, 4-amino-2-(2,6-dioxo-piperidin-3-yl)-5-hydroxy-isoindole-1,3-dione, 4-amino-2-(2,6-dioxo-piperidin-3-yl)-6-hydroxy-isoindole-1,3-dione, or 4-amino-2-(2,6-dioxo-piperidin-3-yl)-7-hydroxy-isoindole-1,3-dione; or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-5-hydroxy-isoindole-1,3-dione, 4-amino-2-(2,6-dioxo-piperidin-3-yl)-6-hydroxy-isoindole-1,3-dione, or 4-amino-2-(2,6-dioxo-piperidin-3-yl)-7-hydroxy-isoindole-1,3-dione; or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-5-hydroxy-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-6-hydroxy-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-7-hydroxy-isoindole-1,3-dione, or an enantiomer or a mixture of enantiomers thereof; or a pharmaceutically acceptable salt, solvate, hydrate, or polymorph thereof.

In certain embodiments, when $R^1$ is a protected hydroxyl, the process provided herein further comprises a step of removing the hydroxyl protecting group to form hydroxyl. In certain embodiments, the deprotection is performed with an acid. In certain embodiments, the acid is a Lewis acid. In certain embodiments, the acid is $AlCl_3$, $AlBr_3$, $BCl_3$, or $BBr_3$. In certain embodiments, the acid is $BCl_3$ or $BBr_3$.

In one embodiment, the process provided herein for preparing an isoindoline-1,3-dione compound of Formula I, or an enantiomer or a mixture of enantiomers thereof; or a pharmaceutically acceptable salt, solvate, hydrate, or polymorph thereof; comprises the steps of:

(i) reacting a compound of Formula IIa with (a) a 3-aminopiperidine-2,6-dione salt, in one embodiment, 3-aminopiperidine-2,6-dione hydrochloride, or an enantiomer or a mixture of enantiomers thereof; in the presence of (b) a base, in one embodiment, an organic base, in another embodiment, pyridine; at (c) an elevated temperature, in one embodiment, about 100° C.; to form the compound of Formula II; and (ii) deprotecting the compound of Formula II to form the compound of Formula I.

In another embodiment, the process provided herein is for preparing 4-amino-2-(2,6-dioxopiperidin-3-yl)-7-hydroxy-isoindoline-1,3-dione:

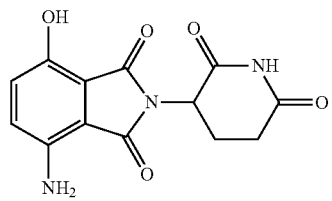

or an enantiomer or a mixture of enantiomers thereof; or a pharmaceutically acceptable salt, solvate, hydrate, or polymorph thereof;
comprising the steps of:

(i) reacting dimethyl 3-(tert-butoxycarbonylamino)-6-hydroxyphthalate:

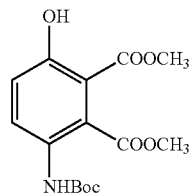 [SMILES: COC(=O)c1c(O)ccc(NC(=O)OC(C)(C)C)c1C(=O)OC]

with 3-aminopiperidine-2,6-dione hydrochloride, or an enantiomer or a mixture of enantiomers thereof; to form tert-butyl 2-(2,6-dioxopiperidin-3-yl)-7-hydroxy-1,3-dioxoisoindolin-4-ylcarbamate:

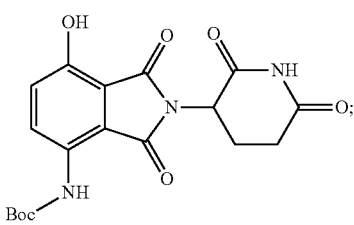 [SMILES: CC(C)(C)OC(=O)Nc1ccc(O)c2c1C(=O)N(C1CCC(=O)NC1=O)C2=O]

and (ii) deprotecting tert-butyl 2-(2,6-dioxopiperidin-3-yl)-7-hydroxy-1,3-dioxoisoindolin-4-ylcarbamate to form 4-amino-2-(2,6-dioxopiperidin-3-yl)-7-hydroxyisoindoline-1,3-dione.

In yet another embodiment, the process for preparing 4-amino-2-(2,6-dioxopiperidin-3-yl)-7-hydroxyisoindoline-1,3-dione, or an enantiomer or a mixture of enantiomers thereof; or a pharmaceutically acceptable salt, solvate, hydrate, or polymorph thereof; comprises the steps of:

(i) reacting dimethyl 3-(tert-butoxycarbonylamino)-6-hydroxyphthalate with 3-aminopiperidine-2,6-dione hydrochloride, or an enantiomer or a mixture of enantiomers thereof; in the presence of (a) a base, in one embodiment, an organic base, in another embodiment, pyridine; at (b) an elevated temperature, in one embodiment, about 100° C.; to form tert-butyl 2-(2,6-dioxopiperidin-3-yl)-7-hydroxy-1,3-dioxoisoindolin-4-ylcarbamate; and (ii) deprotecting tert-butyl 2-(2,6-dioxopiperidin-3-yl)-7-hydroxy-1,3-dioxoisoindolin-4-ylcarbamate with an acid, in one embodiment, trifluoroacetic acid, to form 4-amino-2-(2,6-dioxopiperidin-3-yl)-7-hydroxyisoindoline-1,3-dione.

In one embodiment, the process for preparing 4-amino-2-(2,6-dioxopiperidin-3-yl)-7-hydroxyisoindoline-1,3-dione further comprises a process for preparing dimethyl 3-(tert-butoxycarbonylamino)-6-hydroxyphthalate, which comprises the step of reacting tert-butyl furan-2-ylcarbamate with dimethyl but-2-ynedioate via the Diels-Alder reaction to form dimethyl 3-(tert-butoxycarbonylamino)-6-hydroxyphthalate; wherein the methyl groups each function as a carboxyl protecting group, and the Boc group functions an amino protecting group. Thus, other suitable carboxyl protecting groups can be employed in the place of the methyl groups; and other suitable amino protecting groups can be used in the place of the Boc group. In certain embodiments, the carboxyl protecting groups are each independently methyl, ethyl, tert-butyl, phenyl, or benzyl. In certain embodiments, the carboxyl protecting groups are each independently methyl, ethyl, phenyl, or benzyl. In certain embodiments, the carboxyl protecting groups are methyl. In certain embodiments, the amino protecting group is Boc, Cbz, or Fmoc. In certain embodiments, the amino protecting group is Boc.

In certain embodiments, the Diels-Alder reaction is performed in a solvent. In certain embodiments, the solvent is an organic solvent. In certain embodiments, the solvent is toluene.

In certain embodiments, the Diels-Alder reaction is performed at a temperature ranging from about 0 to about 150° C., from about 10 to about 100° C., or from about 25 to about 75° C. In certain embodiments, the Diels-Alder reaction is performed at about 25, about 30, about 35, about 40, about 45, about 50, about 55, or about 60° C. In certain embodiments, the Diels-Alder reaction is performed at about 45° C.

In another embodiment, the process for preparing 4-amino-2-(2,6-dioxopiperidin-3-yl)-7-hydroxyisoindoline-1,3-dione further comprises a process for preparing tert-butyl furan-2-ylcarbamate, which comprises the step of reacting furan-2-carboxylic acid with an azide reagent, in one embodiment, diphenyl phosphorazidate (DPPA), in the presence of tert-butyl alcohol to form tert-butyl furan-2-ylcarbamate; wherein the Boc group functions as an amino protecting group. Thus, other suitable amino protecting group can also be used in the place of the Boc group. In certain embodiments, the amino protecting group is Boc, Cbz, or Fmoc. For example, Cbz and Fmoc can be formed by using benzyl alcohol or (9H-fluoren-9-yl)methanol, respectively, in the place of tert-butanol in the reaction.

In certain embodiments, the reaction of furan-2-carboxylic acid with an azide reagent is performed in a solvent. In certain embodiments, the solvent is an organic solvent. In certain embodiments, the solvent is an alcohol. In certain embodiments, the solvent is tert-butanol, benzyl alcohol, or (9H-fluoren-9-yl)methanol. In certain embodiments, the solvent is tert-butanol. In certain embodiments, the solvent is benzyl alcohol. In certain embodiments, the solvent is (9H-fluoren-9-yl)methanol.

In certain embodiments, the reaction of furan-2-carboxylic acid with an azide reagent is performed at an elevated temperature. In certain embodiments, the temperature is ranging from about 30 to about 150° C., from about 40 to about 125° C., or from about 50 to about 100° C. In certain embodiments, the temperature is about 50, about 60, about 70, about 80, about 85, about 90, about 100° C. In certain embodiments, the temperature is about 80 or about 85° C.

In yet another embodiment, the process provided herein for preparing 4-amino-2-(2,6-dioxopiperidin-3-yl)-7-hydroxyisoindoline-1,3-dione, or an enantiomer or a mixture of enantiomers thereof; or a pharmaceutically acceptable salt, solvate, hydrate, or polymorph thereof; comprises the steps of:

(i) reacting furan-2-carboxylic acid with diphenyl phosphorazidate in the presence of an alcohol, in one embodiment, t-butanol, to form a 2-protected aminofuran;

(ii) reacting the 2-protected aminofuran with a carboxyl protected but-2-ynedioic acid via the Diels-Alder reaction to form a carboxyl protected 3-protected amino-6-hydroxyphthalic acid;

(iii) reacting the carboxyl protected 3-protected amino-6-hydroxyphthalic acid with 3-aminopiperidine-2,6-dione hydrochloride, or an enantiomer or a mixture of enantiomers thereof; to form a 4-protected amino-2-(2,6-dioxopiperidin-3-yl)-7-hydroxyisoindoline-1,3-dione; and (iv) deprotecting the 4-protected amino-2-(2,6-dioxopiperidin-3-yl)-7-hydroxyisoindoline-1,3-dione to form 4-amino-2-(2,6-dioxopiperidin-3-yl)-7-hydroxyisoindoline-1,3-dione.

In still another embodiment, the process provided herein for preparing 4-amino-2-(2,6-dioxopiperidin-3-yl)-7-hydroxyisoindoline-1,3-dione, or an enantiomer or a mixture of enantiomers thereof; or a pharmaceutically acceptable salt, solvate, hydrate, or polymorph thereof; comprises the steps of:

(i) reacting furan-2-carboxylic acid with diphenyl phosphorazidate and tert-butyl alcohol to form tert-butyl furan-2-ylcarbamate;

(ii) reacting tert-butyl furan-2-ylcarbamate with dimethyl but-2-ynedioate via the Diels-Alder reaction to form dimethyl 3-(tert-butoxycarbonylamino)-6-hydroxyphthalate;

(iii) reacting dimethyl 3-(tert-butoxycarbonylamino)-6-hydroxyphthalate with 3-aminopiperidine-2,6-dione hydrochloride, or an enantiomer or a mixture of enantiomers thereof; in the presence of (a) a base, in one embodiment, an organic base, in another embodiment, pyridine; in (b) a solvent, in one embodiment, pyridine; at (c) an elevated temperature, in one embodiment, about 100° C.; to form tert-butyl 2-(2,6-dioxopiperidin-3-yl)-7-hydroxy-1,3-dioxoisoindolin-4-ylcarbamate; and (iv) deprotecting tert-butyl 2-(2,6-dioxopiperidin-3-yl)-7-hydroxy-1,3-dioxoisoindolin-4-ylcarbamate with trifluoroacetic acid to form 4-amino-2-(2,6-dioxopiperidin-3-yl)-7-hydroxyisoindoline-1,3-dione.

In yet another embodiment, provided herein is a process for preparing an isoindoline-1,3-dione compound of Formula I:

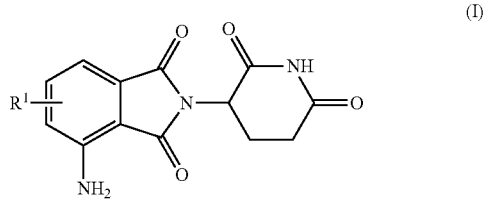

or an enantiomer or a mixture of enantiomers thereof; or a pharmaceutically acceptable salt, solvate, hydrate, or polymorph thereof;
comprising the step of reducing a compound of Formula III:

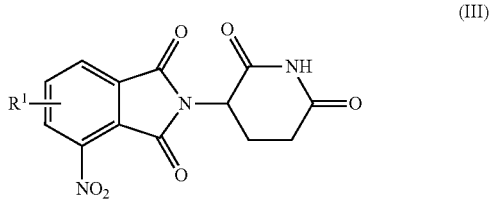

to form the compound of Formula I;
wherein $R^1$ is hydroxyl or $-OR^{1a}$; and $R^{1a}$ is a hydroxyl protecting group.

In certain embodiments, the reduction of the compound of Formula III is performed via catalytic hydrogenation. In certain embodiments, the reduction of the compound of Formula III is performed using a reducing agent.

In certain embodiments, the reduction is performed in a solvent. In certain embodiments, the solvent is an organic solvent. In certain embodiments, the solvent is tetrahydrofuran.

In certain embodiments, the reduction is performed at a temperature ranging from about 0 to about 150° C.; from about 10 to about 100° C., from about 15 to about 50° C. In certain embodiments, the temperature is about 10, about 15, about 20, about 25, about 30 about 35, about 40, about 45, or about 50° C. In certain embodiments, the temperature is about 25° C. In certain embodiments, the temperature is room temperature.

In certain embodiments, $R^1$ is hydroxyl. In certain embodiments, $R^1$ is $-OR^{1a}$, wherein $R^{1a}$ is a hydroxyl protecting group. In certain embodiments, $R^{1a}$ is $C_{1-6}$ alkyl. In certain embodiments, $R^{1a}$ is methyl, ethyl, propyl, t-butyl, or benzyl. In certain embodiments, $R^{1a}$ is methyl or isopropyl. In certain embodiments, $R^{1a}$ is methyl. In certain embodiments, $R^{1a}$ is isopropyl. In certain embodiments, $R^1$ is hydroxyl, methoxy, ethoxy, isopropoxy, t-butoxy, or benzyloxy. In certain embodiments, $R^1$ is hydroxyl or isopropoxy. In certain embodiments, $R^1$ is hydroxyl. In certain embodiments, $R^1$ is isopropoxy.

In certain embodiments, the compound of Formula III is 2-(2,6-dioxo-piperidin-3-yl)-5-hydroxy-4-nitro-isoindole-1,3-dione, 2-(2,6-dioxo-piperidin-3-yl)-6-hydroxy-4-nitro-isoindole-1,3-dione, 2-(2,6-dioxo-piperidin-3-yl)-7-hydroxy-4-nitro-isoindole-1,3-dione, 2-(2,6-dioxo-piperidin-3-yl)-5-methoxy-4-nitro-isoindole-1,3-dione, 2-(2,6-dioxo-piperidin-3-yl)-6-methoxy-4-nitro-isoindole-1,3-dione, or 2-(2,6-dioxo-piperidin-3-yl)-7-methoxy-4-nitro-isoindole-1,3-dione; or an enantiomer or a mixture of enantiomers thereof.

In certain embodiments, the compound of Formula III is 2-(2,6-dioxo-piperidin-3-yl)-5-hydroxy-4-nitro-isoindole-1,3-dione, 2-(2,6-dioxo-piperidin-3-yl)-6-hydroxy-4-nitro-isoindole-1,3-dione, or 2-(2,6-dioxo-piperidin-3-yl)-7-hydroxy-4-nitro-isoindole-1,3-dione; or an enantiomer or a mixture of enantiomers thereof. In certain embodiments, the compound of Formula III is 2-(2,6-dioxo-piperidin-3-yl)-5-hydroxy-4-nitro-isoindole-1,3-dione, or an enantiomer or a mixture of enantiomers thereof. In certain embodiments, the compound of Formula III is 2-(2,6-dioxo-piperidin-3-yl)-6-hydroxy-4-nitro-isoindole-1,3-dione, or an enantiomer or a mixture of enantiomers thereof. In certain embodiments, the compound of Formula III is 2-(2,6-dioxo-piperidin-3-yl)-7-hydroxy-4-nitro-isoindole-1,3-dione, or an enantiomer or a mixture of enantiomers thereof.

In certain embodiments, the compound of Formula III is 2-(2,6-dioxo-piperidin-3-yl)-5-methoxy-4-nitro-isoindole-1,3-dione, 2-(2,6-dioxo-piperidin-3-yl)-6-methoxy-4-nitro-isoindole-1,3-dione, or 2-(2,6-dioxo-piperidin-3-yl)-7-methoxy-4-nitro-isoindole-1,3-dione; or an enantiomer or a mixture of enantiomers thereof. In certain embodiments, the compound of Formula III is 2-(2,6-dioxo-piperidin-3-yl)-5-methoxy-4-nitro-isoindole-1,3-dione, or an enantiomer or a mixture of enantiomers thereof. In certain embodiments, the compound of Formula III is 2-(2,6-dioxo-piperidin-3-yl)-6-methoxy-4-nitro-isoindole-1,3-dione, or an enantiomer or a mixture of enantiomers thereof. In certain embodiments, the compound of Formula III is 2-(2,6-dioxo-piperidin-3-yl)-7-methoxy-4-nitro-isoindole-1,3-dione, or an enantiomer or a mixture of enantiomers thereof.

In certain embodiments, the compound of Formula I is 4-amino-2-(2,6-dioxo-piperidin-3-yl)-5-hydroxy-isoindole-1,3-dione, 4-amino-2-(2,6-dioxo-piperidin-3-yl)-6-hydroxy-isoindole-1,3-dione, or 4-amino-2-(2,6-dioxo-piperidin-3-yl)-7-hydroxy-isoindole-1,3-dione; or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-5-hydroxy-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-6-hydroxy-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-7-hydroxy-isoindole-1,3-dione, or an enantiomer or a mixture of enantiomers thereof; or a pharmaceutically acceptable salt, solvate, hydrate, or polymorph thereof.

In certain embodiments, the compound of Formula I is 4-amino-2-(2,6-dioxo-piperidin-3-yl)-5-methoxy-isoindole-1,3-dione, 4-amino-2-(2,6-dioxo-piperidin-3-yl)-6-methoxy-isoindole-1,3-dione, or 4-amino-2-(2,6-dioxo-piperidin-3-yl)-7-methoxy-isoindole-1,3-dione; or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-5-methoxy-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-6-methoxy-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-7-methoxy-isoindole-1,3-dione, or an enantiomer or a mixture of enantiomers thereof; or a pharmaceutically acceptable salt, solvate, hydrate, or polymorph thereof.

In certain embodiments, when $R^1$ is a protected hydroxyl, the process provided herein further comprises a step of removing the hydroxyl protecting group to form hydroxyl. In certain embodiments, the deprotection is performed with an acid. In certain embodiments, the acid is a Lewis acid. In certain embodiments, the acid is $AlCl_3$, $AlBr_3$, $BCl_3$, or $BBr_3$. In certain embodiments, the acid is $BCl_3$ or $BBr_3$.

In one embodiment, the process provided herein for preparing an isoindoline-1,3-dione compound of Formula I, or an enantiomer or a mixture of enantiomers thereof; or a pharmaceutically acceptable salt, solvate, hydrate, or polymorph thereof; which comprises the step of reducing a compound of Formula III with hydrogen in the presence of (i) a catalyst, in one embodiment, Pd/C; in (ii) a solvent, in one embodiment, THF; to form the compound of Formula I.

In another embodiment, the process provided herein is for preparing 4-amino-2-(2,6-dioxopiperidin-3-yl)-6-hydroxy-isoindoline-1,3-dione:

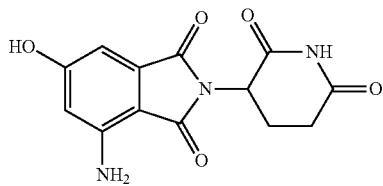 [SMILES: Nc1cc(O)cc2c1C(=O)N(C1CCC(=O)NC1=O)C2=O]

or an enantiomer or a mixture of enantiomers thereof; or a pharmaceutically acceptable salt, solvate, hydrate, or polymorph thereof;
comprising the step of reducing 2-(2,6-dioxopiperidin-3-yl)-6-hydroxy-4-nitroisoindoline-1,3-dione:

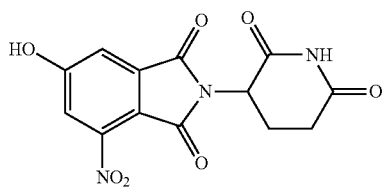

to form 4-amino-2-(2,6-dioxopiperidin-3-yl)-6-hydroxy-isoindoline-1,3-dione.

In yet another embodiment, the process provided herein for preparing 4-amino-2-(2,6-dioxopiperidin-3-yl)-6-hydroxy-isoindoline-1,3-dione, or an enantiomer or a mixture of enantiomers thereof; or a pharmaceutically acceptable salt, solvate, hydrate, or polymorph thereof; comprises the step of reducing 2-(2,6-dioxopiperidin-3-yl)-6-hydroxy-4-nitroisoindoline-1,3-dione with hydrogen in the presence of (i) a catalyst, in one embodiment, Pd/C; in (ii) a solvent, in one embodiment, THF; to form 4-amino-2-(2,6-dioxopiperidin-3-yl)-6-hydroxyisoindoline-1,3-dione.

In one embodiment, the process for preparing 4-amino-2-(2,6-dioxopiperidin-3-yl)-6-hydroxyisoindoline-1,3-dione further comprises a process for preparing 2-(2,6-dioxopiperidin-3-yl)-6-hydroxy-4-nitroisoindoline-1,3-dione, which comprises the steps of (i) coupling 6-isopropoxy-4-nitroisobenzofuran-1,3-dione with 3-aminopiperidine-2,6-dione to form 2-(2,6-dioxopiperidin-3-yl)-6-isopropoxy-4-nitroisoindoline-1,3-dione; and (ii) deprotecting 2-(2,6-dioxopiperidin-3-yl)-6-isopropoxy-4-nitroisoindoline-1,3-dione, in one embodiment, in the presence of $BCl_3$, to form 2-(2,6-dioxopiperidin-3-yl)-6-hydroxy-4-nitroisoindoline-1,3-dione; wherein the isopropyl group functions as a hydroxyl group. Thus, other suitable hydroxyl protecting can also be employed in the place of the isopropyl group. In certain embodiments, the hydroxyl protecting group is methyl, ethyl, isopropyl, benzyl, or a silyl group. In certain embodiments, the hydroxyl protecting group is methyl, ethyl, isopropyl, or benzyl. In certain embodiments, the hydroxyl protecting group is methyl or isopropyl. In certain embodiments, the hydroxyl protecting group is methyl. In certain embodiments, the hydroxyl protecting group is isopropyl.

In certain embodiments, the coupling reaction is performed in a solvent. In certain embodiments, the solvent is an organic solvent. In certain embodiments, the solvent is an acid. In certain embodiments, the solvent is acetic acid.

In certain embodiments, the coupling reaction is performed at an elevated temperature. In certain embodiments, the temperature is ranging from about 30 to about 150° C., from about 50 to about 125° C., or from about 75 to about 125° C. In certain embodiments, the coupling temperature is about 80, about 90, about 100, about 110, about 120° C. In certain embodiments, the coupling temperature is about 100° C.

In certain embodiments, the deprotection is performed in a solvent. In certain embodiments, the solvent is an organic solvent. In certain embodiments, the solvent is dichloromethane.

In certain embodiments, the deprotection is performed at a temperature ranging from about 0 to about 150° C.; from about 10 to about 100° C., or from about 15 to about 50° C. In certain embodiments, the temperature is about 10, about 15, about 20, about 25, about 30, about 35, about 40, about 45, or about 50° C. In certain embodiments, the temperature is about 25° C. In certain embodiments, the temperature is room temperature.

In another embodiment, the process for preparing 4-amino-2-(2,6-dioxopiperidin-3-yl)-6-hydroxyisoindoline-1,3-dione further comprises a process for preparing 6-isopropoxy-4-nitroisobenzofuran-1,3-dione, which comprises the step of reacting 5-isopropoxy-3-nitrophthalic acid with a coupling reagent to form 6-isopropoxy-4-nitroisobenzofuran-1,3-dione; wherein the isopropyl group functions as a hydroxyl group. Thus, other suitable hydroxyl protecting can also be employed in the place of the isopropyl group. In certain embodiments, the hydroxyl protecting group is methyl, ethyl, isopropyl, benzyl, or a silyl group. In certain embodiments, the hydroxyl protecting group is methyl, ethyl, isopropyl, or benzyl. In certain embodiments, the hydroxyl protecting group is methyl or isopropyl. In certain embodiments, the hydroxyl protecting group is methyl. In certain embodiments, the hydroxyl protecting group is isopropyl.

In certain embodiments, the coupling reagent is an anhydride. In certain embodiments, the coupling reagent is acetic anhydride. In certain embodiments, the coupling reagent is CDI or EDCI.

In certain embodiments, the cyclization reaction is performed in a solvent. In certain embodiments, the solvent is an organic solvent. In certain embodiments, the solvent is acetic anhydride.

In certain embodiments, the cyclization reaction is performed at an elevated temperature. In certain embodiments, the reaction temperature is ranging from about 50 to about 200° C., from about 75 to about 150° C., or about 100 to about 150° C. In certain embodiments, the reaction temperature is about 100, about 110, about 120, about 130, about 140, or about 150° C. In certain embodiments, the reaction temperature is about 130° C.

In yet another embodiment, the process for preparing 4-amino-2-(2,6-dioxopiperidin-3-yl)-6-hydroxyisoindoline-1,3-dione further comprises a process for preparing 5-isopropoxy-3-nitrophthalic acid, which comprises the step of reacting methyl 5-isopropoxy-2-methyl-3-nitrobenzoate with an oxidant to form 5-isopropoxy-3-nitrophthalic acid; wherein the methyl group on the carboxy group functions as a carboxyl protecting group, and the isopropyl group functions as a hydroxyl group. Thus, other suitable carboxyl protecting groups can also be employed in the place of the methyl group. In certain embodiments, the carboxyl protecting group is methyl, ethyl, tert-butyl, phenyl, or benzyl. In certain embodiments, the carboxyl protecting group is methyl. Other suitable hydroxyl protecting can also be employed in the place of the isopropyl group. In certain embodiments, the hydroxyl protecting group is methyl, ethyl, isopropyl, benzyl, or a silyl group. In certain embodiments, the hydroxyl protecting group is methyl, ethyl, isopropyl, or benzyl. In certain embodiments, the hydroxyl protecting group is methyl or isopropyl. In certain embodiments, the hydroxyl protecting group is methyl. In certain embodiments, the hydroxyl protecting group is isopropyl.

In certain embodiments, the oxidant is $KMnO_4$.

In certain embodiments, the oxidation is performed in the presence of a base. In certain embodiments, the base is an inorganic base. In certain embodiments, the base is sodium hydroxide or potassium hydroxide. In certain embodiments, the base is sodium hydroxide. In certain embodiments, the base is an organic base.

In certain embodiments, the oxidation is performed in a solvent. In certain embodiments, the solvent is an inorganic solvent. In certain embodiments, the solvent is water. In certain embodiments, the solvent is an organic solvent.

In certain embodiments, the oxidation is performed at an elevated temperature. In certain embodiments, the temperature is ranging from about 50 to about 200° C., about 50 to about 150° C., or about 75 to about 125° C. In certain embodiments, the reaction temperature is about 80, about 90, about 100, about 110, or about 120° C. In certain embodiments, the reaction temperature is about 100° C.

In yet another embodiment, the process for preparing 4-amino-2-(2,6-dioxopiperidin-3-yl)-6-hydroxyisoindoline-1,3-dione further comprises a process for preparing methyl 5-isopropoxy-2-methyl-3-nitrobenzoate, which comprises the steps of (i) reacting a 5-borylated methyl 2-methyl-3-nitrobenzoate, in one embodiment, methyl 2-methyl-3-nitro-5-(4,4,5,5-tetramethyl-1,3,2-dioxaborolan-2-yl)benzoate, with an oxidant to form methyl 5-hydroxy-2-methyl-3-nitrobenzoate; and (ii) reacting methyl 5-hydroxy-2-methyl-3-nitrobenzoate with 2-iodopropane in the presence of a base to form methyl 5-isopropoxy-2-methyl-3-nitrobenzoate, wherein the isopropyl group functions as a hydroxyl group. Thus, other suitable hydroxyl protecting can also be employed in the place of the isopropyl group. In certain embodiments, the hydroxyl protecting group is methyl, ethyl, isopropyl, benzyl, or a silyl group. In certain embodiments, the hydroxyl protecting group is methyl, ethyl, isopropyl, or benzyl. In certain embodiments, the hydroxyl protecting group is methyl or isopropyl. In certain embodiments, the hydroxyl protecting group is methyl. In certain embodiments, the hydroxyl protecting group is isopropyl.

In certain embodiments, the oxidant is OXONE®, hydrogen peroxide, or 3-chloroperoxybenzoic acid (mCPBA). In certain embodiments, the oxidant is OXONE®

In certain embodiments, the oxidation is performed in a solvent. In certain embodiments, the solvent is an organic solvent. In certain embodiments, the solvent is acetone.

In certain embodiments, the oxidation is performed at a temperature ranging from about 0 to about 150° C., from about 10 to about 100° C., or from about 15 to about 50° C. In certain embodiments, the temperature is about 10, about 20, about 30, about 40, or about 50° C. In certain embodiments, the temperature is about 25° C. In certain embodiments, the temperature is room temperature.

In certain embodiments, the base used in the alkylation reaction is an inorganic base. In certain embodiments, the base is potassium carbonate. In certain embodiments, the base used in the alkylation reaction is an organic base.

In certain embodiments, the alkylation is performed in a solvent. In certain embodiments, the solvent is an organic solvent. In certain embodiments, the solvent is acetonitrile.

In certain embodiments, the alkylation is performed at an elevated temperature. In certain embodiments, the temperature is ranging from about 30 to about 150° C., from about 30 to about 100° C., or from about 30 to about 50° C. In certain embodiments, the temperature is about 30, about 35, about 40, about 45, about 50, about 55, or about 60° C. In certain embodiments, the temperature is about 45° C.

In yet another embodiment, the process for preparing 4-amino-2-(2,6-dioxopiperidin-3-yl)-6-hydroxyisoindoline-1,3-dione further comprises a process for preparing a 5-borylated methyl 2-methyl-3-nitrobenzoate, in one embodiment, methyl 2-methyl-3-nitro-5-(4,4,5,5-tetramethyl-1,3,2-dioxaborolan-2-yl)benzoate, which comprises the step of reacting methyl 5-bromo-2-methyl-3-nitrobenzoate with a borylation reagent to form the 5-borylated methyl 2-methyl-3-nitrobenzoate.

In certain embodiments, the borylation reagent is bis(pinacolato)diboron, bis(hexylene glycolato)diboron, bis(catecholato)diboron, bis(neopentyl glycolato)diboron, 4,6,6-trimethyl-1,3,2-dioxaborinane, 4,4,5,5-tetramethyl-1,3,2-dioxaborolane, or catecholborane. In certain embodiments, the borylation reagent is bis(pinacolato)diboron.

In certain embodiments, the borylation is performed in the presence of a catalyst. In certain embodiments, the catalyst is a heterogeneous hydrogenation catalyst. In certain embodiments, the catalyst is a homogeneous hydrogenation catalyst. In certain embodiments, the homogeneous catalyst is an iridium-based catalyst. In certain embodiments, the homogeneous catalyst is a palladium-based catalyst. In certain embodiments, the catalyst is $Pd(dppf)Cl_2$. In certain embodiments, the homogeneous catalyst is a platinum-based catalyst. In certain embodiments, the homogeneous catalyst is a rhodium-based catalyst. In certain embodiments, the catalyst is a palladium-based catalyst.

In certain embodiments, the borylation is performed in the presence of a base. In certain embodiments, the base is an inorganic base. In certain embodiments, the base is an organic base. In certain embodiments, the base is potassium acetate.

In certain embodiments, the borylation is performed in a solvent. Irl certain embodiments, the solvent is an organic solvent. In certain embodiments, the solvent is dioxane.

In certain embodiments, the borylation is performed at an elevated temperature. In certain embodiments, the temperature is ranging from about 30 to about 200° C., from about 50 to about 150° C., or from about 75 to about 125° C. In certain embodiments, the temperature is about 80, about 90, about 100, about 110, or about 120° C. In certain embodiments, the temperature is about 100° C.

In yet another embodiment, the process for preparing 4-amino-2-(2,6-dioxopiperidin-3-yl)-6-hydroxyisoindoline-1,3-dione further comprises a process for preparing methyl 5-bromo-2-methyl-3-nitrobenzoate, which comprises the steps of (i) reacting 2-methyl-3-nitrobenzoic acid with a bromination reagent to form 5-bromo-2-methyl-3-nitrobenzoic acid; and (ii) reacting 5-bromo-2-methyl-3-nitrobenzoic acid with methanol to form methyl 5-bromo-2-methyl-3-nitrobenzoate; wherein the methyl group functions a carboxyl protecting group. Thus, other suitable carboxyl protecting groups can also be employed in the place of the methyl group. In certain embodiments, the carboxyl protecting group is methyl, ethyl, tert-butyl, phenyl, or benzyl. In certain embodiments, the carboxyl protecting group is methyl, ethyl, phenyl, or benzyl. In certain embodiments, the carboxyl protecting group is methyl.

In certain embodiments, the bromination reagent is bromine, N-bromosuccinimide (NBS), or 1,3-dibromo-5,5-dimethylhydantoin (DBDMH). In certain embodiments, the bromination reagent is DBDMH.

In certain embodiments, the bromination is performed in a solvent. In certain embodiments, the solvent is an inorganic solvent. In certain embodiments, the solvent is sulfuric acid. In certain embodiments, the solvent is an organic solvent.

In certain embodiments, the bromination is performed at a temperature ranging from about 0 to about 150° C., from about 10 to about 100° C., or from about 15 to about 50° C. In certain embodiments, the temperature is about 10, about 20, about 30, about 40, or about 50° C. In certain embodiments, the temperature is about 25° C. In certain embodiments, the temperature is room temperature.

In certain embodiments, the carboxyl protection is performed in the presence of a coupling reagent. In certain embodiments, the coupling reagent is $SOCl_2$, $POCl_3$, or EDCI. In certain embodiments, the coupling reagent is $SOCl_2$. In certain embodiments, the coupling reagent is $PCl_5$, $COCl_2$, or $C_2O_2Cl_2$ (oxalyl chloride).

In certain embodiments, the carboxyl protection is performed at an elevated temperature. In certain embodiments, the temperature is ranging from about 30 to about 150° C., about 40 to about 100° C., or about 50 to about 105° C. In certain embodiments, the reaction temperature is about 40, about 50, about 60, about 65, about 70, about 80, or about 90° C. In certain embodiments, the reaction temperature is about 65° C.

In yet another embodiment, provided herein is a process for preparing 4-amino-2-(2,6-dioxopiperidin-3-yl)-6-hydroxy-isoindoline-1,3-dione, or an enantiomer or a mixture of enantiomers thereof; or a pharmaceutically acceptable salt, solvate, hydrate, or polymorph thereof; comprising the steps of:

(i) reacting 2-methyl-3-nitrobenzoic acid with a bromination reagent to form 5-bromo-2-methyl-3-nitrobenzoic acid;

(ii) protecting 5-bromo-2-methyl-3-nitrobenzoic acid to form a carboxyl protected 5-bromo-2-methyl-3-nitrobenzoic acid;

(iii) reacting the carboxyl protected 5-bromo-2-methyl-3-nitrobenzoic acid with a borylation reagent to form a carboxyl protected 5-borylated-2-methyl-3-nitrobenzoic acid;

(iv) reacting the carboxyl protected 5-borylated-2-methyl-3-nitrobenzoic acid with an oxidant to form a carboxyl protected 5-hydroxy-2-methyl-3-nitrobenzoic acid;

(v) protecting the carboxyl protected 5-hydroxy-2-methyl-3-nitrobenzoic acid to form a carboxyl protected 5-protected hydroxy-2-methyl-3-nitrobenzoic acid;

(vi) reacting the carboxyl protected 5-protected hydroxy-2-methyl-3-nitrobenzoic acid with an oxidant to form a 5-protected hydroxyl-3-nitrophthalic acid;

(vii) reacting the 5-protected hydroxyl-3-nitrophthalic acid with a coupling reagent to form a 6-protected hydroxyl-4-nitroisobenzofuran-1,3-dione;

(viii) reacting the 6-protected hydroxyl-4-nitroisobenzofuran-1,3-dione with 3-aminopiperidine-2,6-dione to form a 2-(2,6-dioxopiperidin-3-yl)-6-protected hydroxyl-4-nitroisoindoline-1,3-dione;

(ix) deprotecting the 2-(2,6-dioxopiperidin-3-yl)-6-protected hydroxyl-4-nitroisoindoline-1,3-dione to form 2-(2,6-dioxopiperidin-3-yl)-6-hydroxy-4-nitroisoindoline-1,3-dione; and (x) reducing 2-(2,6-dioxopiperidin-3-yl)-6-hydroxy-4-nitroisoindoline-1,3-dione to form 4-amino-2-(2,6-dioxopiperidin-3-yl)-6-hydroxyisoindoline-1,3-dione.

In yet another embodiment, the process for preparing 4-amino-2-(2,6-dioxopiperidin-3-yl)-6-hydroxyisoindoline-1,3-dione comprises the steps of:

(i) reacting 2-methyl-3-nitrobenzoic acid with a bromination reagent, in one embodiment, 1,3-dibromo-5,5-dimethylhydantoin, to form 5-bromo-2-methyl-3-nitrobenzoic acid;

(ii) reacting 5-bromo-2-methyl-3-nitrobenzoic acid with methanol to form methyl 5-bromo-2-methyl-3-nitrobenzoate;

(iii) reacting methyl 5-bromo-2-methyl-3-nitrobenzoate with a borylation reagent to form methyl 5-borylated-2-methyl-3-nitrobenzoate;

(iv) reacting methyl 5-borylated-2-methyl-3-nitrobenzoate with an oxidant, in one embodiment, OXONE®, to form methyl 5-hydroxy-2-methyl-3-nitrobenzoate;

(v) reacting methyl 5-hydroxy-2-methyl-3-nitrobenzoate with 2-iodopropane in the presence of a base to form methyl 5-isopropoxy-2-methyl-3-nitrobenzoate;

(vi) reacting methyl 5-isopropoxy-2-methyl-3-nitrobenzoate with an oxidant, in one embodiment, $KMnO_4$, to form 5-isopropoxy-3-nitrophthalic acid;

(vii) reacting 5-isopropoxy-3-nitrophthalic acid with a coupling reagent, in one embodiment, acetic anhydride, to form 6-isopropoxy-4-nitroisobenzofuran-1,3-dione;

(viii) reacting 6-isopropoxy-4-nitroisobenzofuran-1,3-dione with 3-aminopiperidine-2,6-dione to form 2-(2,6-dioxopiperidin-3-yl)-6-isopropoxy-4-nitroisoindoline-1,3-dione;

(ix) deprotecting 2-(2,6-dioxopiperidin-3-yl)-6-isopropoxy-4-nitroisoindoline-1,3-dione, in one embodiment, with $BCl_3$, to form 2-(2,6-dioxopiperidin-3-yl)-6-hydroxy-4-nitroisoindoline-1,3-dione; and (x) reducing 2-(2,6-dioxopiperidin-3-yl)-6-hydroxy-4-nitroisoindoline-1,3-dione to form 4-amino-2-(2,6-dioxopiperidin-3-yl)-6-hydroxyisoindoline-1,3-dione.

In still another embodiment, the process for preparing 4-amino-2-(2,6-dioxopiperidin-3-yl)-6-hydroxyisoindoline-1,3-dione comprises the steps of:

(i) reacting 2-methyl-3-nitrobenzoic acid with a bromination reagent, in one embodiment, 1,3-dibromo-5,5-dimethylhydantoin, to form 5-bromo-2-methyl-3-nitrobenzoic acid;

(ii) reacting 5-bromo-2-methyl-3-nitrobenzoic acid with methanol to form methyl 5-bromo-2-methyl-3-nitrobenzoate;

(iii) reacting methyl 5-bromo-2-methyl-3-nitrobenzoate with bis(pinacolato)diboron to form methyl 2-methyl-3-nitro-5-(4,4,5,5-tetramethyl-1,3,2-dioxaborolan-2-yl)benzoate;

(iv) reacting methyl 2-methyl-3-nitro-5-(4,4,5,5-tetramethyl-1,3,2-dioxaborolan-2-yl)benzoate with an oxidant, in one embodiment, OXONE®, to form methyl 5-hydroxy-2-methyl-3-nitrobenzoate;

(v) reacting methyl 5-hydroxy-2-methyl-3-nitrobenzoate with 2-iodopropane in the presence of a base to form methyl 5-isopropoxy-2-methyl-3-nitrobenzoate;

(vi) reacting methyl 5-isopropoxy-2-methyl-3-nitrobenzoate with an oxidant, in one embodiment, KMnO$_4$, to form 5-isopropoxy-3-nitrophthalic acid;

(vii) reacting 5-isopropoxy-3-nitrophthalic acid with a coupling reagent, in one embodiment, acetic anhydride, to form 6-isopropoxy-4-nitroisobenzofuran-1,3-dione;

(viii) reacting 6-isopropoxy-4-nitroisobenzofuran-1,3-dione with 3-aminopiperidine-2,6-dione to form 2-(2,6-dioxopiperidin-3-yl)-6-isopropoxy-4-nitroisoindoline-1,3-dione;

(ix) deprotecting 2-(2,6-dioxopiperidin-3-yl)-6-isopropoxy-4-nitroisoindoline-1,3-dione, in one embodiment, with BCl$_3$, to form 2-(2,6-dioxopiperidin-3-yl)-6-hydroxy-4-nitroisoindoline-1,3-dione; and (x) reducing 2-(2,6-dioxopiperidin-3-yl)-6-hydroxy-4-nitroisoindoline-1,3-dione to form 4-amino-2-(2,6-dioxopiperidin-3-yl)-6-hydroxyisoindoline-1,3-dione.

In yet another embodiment, the process provided herein is for preparing 4-amino-2-(2,6-dioxopiperidin-3-yl)-5-hydroxyisoindoline-1,3-dione:

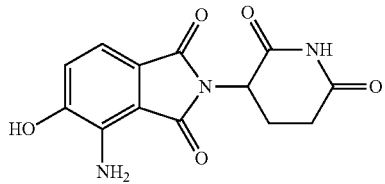

or an enantiomer or a mixture of enantiomers thereof; or a pharmaceutically acceptable salt, solvate, hydrate, or polymorph thereof;
comprising the steps of:

(i) reducing 2-(2,6-dioxopiperidin-3-yl)-5-methoxy-4-nitroisoindoline-1,3-dione:

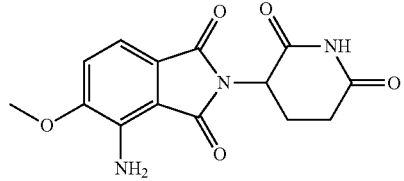 [SMILES: COc1ccc2c(c1N)C(=O)N(C1CCC(=O)NC1=O)C2=O]

to form 4-amino-2-(2,6-dioxopiperidin-3-yl)-5-methoxyisoindoline-1,3-dione; and (ii) deprotecting 4-amino-2-(2,6-dioxopiperidin-3-yl)-5-methoxyisoindoline-1,3-dione, in one embodiment, with BBr$_3$, to form 4-amino-2-(2,6-dioxopiperidin-3-yl)-5-hydroxyisoindoline-1,3-dione.

In yet another embodiment, the process provided herein for preparing 4-amino-2-(2,6-dioxopiperidin-3-yl)-5-hydroxyisoindoline-1,3-dione, or an enantiomer or a mixture of enantiomers thereof; or a pharmaceutically acceptable salt, solvate, hydrate, or polymorph thereof; comprises the steps of (i) reducing 2-(2,6-dioxopiperidin-3-yl)-5-methoxy-4-nitroisoindoline-1,3-dione with hydrogen in the presence of (a) a catalyst, in one embodiment, Pd/C; in (b) a solvent, in one embodiment, DMF; to form 4-amino-2-(2,6-dioxopiperidin-3-yl)-5-methoxyisoindoline-1,3-dione; and (ii) reacting form 4-amino-2-(2,6-dioxopiperidin-3-yl)-5-methoxyisoindoline-1,3-dione with BBr$_3$ to 4-amino-2-(2,6-dioxopiperidin-3-yl)-5-hydroxyisoindoline-1,3-dione.

In one embodiment, the process for preparing 4-amino-2-(2,6-dioxopiperidin-3-yl)-5-hydroxyisoindoline-1,3-dione further comprises a process for preparing 2-(2,6-dioxopiperidin-3-yl)-5-methoxy-4-nitroisoindoline-1,3-dione, which comprises reacting 4-methoxy-3-nitro-phthalic acid with 3-aminopiperidine-2,6-dione, in one embodiment, in the presence of a coupling reagent, to form 2-(2,6-dioxopiperidin-3-yl)-5-methoxy-4-nitroisoindoline-1,3-dione; wherein the methyl group on the methoxy group functions as a hydroxyl protecting group. Thus, other suitable hydroxyl protecting can also be employed in the place of the methyl group. In certain embodiments, the hydroxyl protecting group is methyl, ethyl, isopropyl, benzyl, or a silyl group. In certain embodiments, the hydroxyl protecting group is methyl, ethyl, isopropyl, or benzyl. In certain embodiments, the hydroxyl protecting group is methyl or isopropyl. In certain embodiments, the hydroxyl protecting group is methyl. In certain embodiments, the hydroxyl protecting group is isopropyl.

In certain embodiments, the coupling reaction is performed in the presence of a base. In certain embodiments, the base is an organic base. In certain embodiments, the base is triethylamine. In certain embodiments, the base is an inorganic base.

In certain embodiments, the coupling reaction is performed in the presence of a coupling reagent. In certain embodiments, the coupling reagent is an anhydride. In certain embodiments, the coupling reagent is acetic anhydride. In certain embodiments, the coupling reagent is CDI or EDCI.

In another embodiment, the process for preparing 4-amino-2-(2,6-dioxopiperidin-3-yl)-5-hydroxyisoindoline-1,3-dione further comprises a process for preparing 4-methoxy-3-nitro-phthalic acid, which comprises hydrolyzing 4-methoxy-3-nitro-phthalic acid dimethyl ester to form 4-methoxy-3-nitro-phthalic acid; wherein the methyl group on the methoxy group functions as a hydroxyl protecting group and the two methyl groups on the methyl ester groups each function as a carboxyl protecting group. Thus, other suitable hydroxyl and carboxyl protecting groups can be used in the place of the methyl groups. In certain embodiments, the hydroxyl protecting group is methyl, ethyl, isopropyl, benzyl, or a silyl group. In certain embodiments, the hydroxyl protecting group is methyl, ethyl, isopropyl, or benzyl. In certain embodiments, the hydroxyl protecting group is methyl or isopropyl. In certain embodiments, the hydroxyl protecting group is methyl. In certain embodiments, the hydroxyl protecting group is isopropyl. In certain embodiments, the carboxyl protecting groups are each independently methyl, ethyl, tert-butyl, phenyl, or benzyl. In certain embodiments, the carboxyl protecting groups are each independently methyl, ethyl, phenyl, or benzyl. In certain embodiments, the carboxyl protecting groups are methyl.

In certain embodiments, the hydrolysis is performed in presence of a base. In certain embodiments, the base is an inorganic base. In certain embodiments, the base is sodium hydroxide. In certain embodiments, the base is an organic base.

In certain embodiments, the hydrolysis is performed in a solvent. In certain embodiments, the solvent is an inorganic solvent. In certain embodiments, the solvent is an organic solvent. In certain embodiments, the solvent is a mixture of water and methanol.

In yet another embodiment, the process for preparing 4-amino-2-(2,6-dioxopiperidin-3-yl)-5-hydroxyisoindoline-1,3-dione further comprises a process for preparing 4-methoxy-3-nitro-phthalic acid dimethyl ester, which comprises (i) oxidizing 2-methoxy-1-nitro-naphthalene with an oxidant, in one embodiment, a mixture of $RuO_4$ and $NaIO_4$, to form 4-methoxy-3-nitro-phthalic acid; and (ii) reacting 4-methoxy-3-nitro-phthalic acid with methyl iodide in the presence of a base, in one embodiment, sodium bicarbonate, to form 4-methoxy-3-nitro-phthalic acid dimethyl ester; wherein the methyl groups on the carboxyl groups each function as a carboxyl protecting group. Thus, other suitable carboxyl protecting groups can also be used in the place of the methyl groups. In certain embodiments, the carboxyl protecting groups are each independently methyl, ethyl, tert-butyl, phenyl, or benzyl. In certain embodiments, the carboxyl protecting groups are each independently methyl, ethyl, phenyl, or benzyl. In certain embodiments, the carboxyl protecting groups are methyl.

In yet another embodiment, the process for preparing 4-amino-2-(2,6-dioxopiperidin-3-yl)-5-hydroxyisoindoline-1,3-dione further comprises a process for preparing 2-methoxy-1-nitro-naphthalene, which comprises the step of reacting 1-nitro-naphthalen-2-ol with methyl iodide, in one embodiment, in the presence of a base, in another embodiment, in the presence of potassium carbonate, to form 2-methoxy-1-nitro-naphthalene; wherein the methyl group functions as a hydroxyl protecting group. Thus, other suitable hydroxyl protecting groups can also be used in the place of the methyl group. In certain embodiments, the hydroxyl protecting group is methyl, ethyl, isopropyl, benzyl, or a silyl group. In certain embodiments, the hydroxyl protecting group is methyl, ethyl, isopropyl, or benzyl. In certain embodiments, the hydroxyl protecting group is methyl or isopropyl. In certain embodiments, the hydroxyl protecting group is methyl. In certain embodiments, the hydroxyl protecting group is isopropyl.

In yet another embodiment, provided herein is a process for preparing 4-amino-2-(2,6-dioxopiperidin-3-yl)-5-hydroxyisoindoline-1,3-dione, or an enantiomer or a mixture of enantiomers thereof; or a pharmaceutically acceptable salt, solvate, hydrate, or polymorph thereof; comprising the steps of:

(i) protecting 1-nitro-naphthalen-2-ol to form 2-protected hydroxyl-1-nitro-naphthalene;

(ii) oxidizing 2-protected hydroxyl-1-nitro-naphthalene with an oxidant to form 4-protected hydroxyl-3-nitro-phthalic acid;

(iii) reacting 4-protected hydroxyl-3-nitro-phthalic acid with 3-aminopiperidine-2,6-dione to form 2-(2,6-dioxopiperidin-3-yl)-5-protected hydroxyl-4-nitroisoindoline-1,3-dione;

(iv) reducing 2-(2,6-dioxopiperidin-3-yl)-5-protected hydroxyl-4-nitroisoindoline-1,3-dione to form 4-amino-2-(2,6-dioxopiperidin-3-yl)-5-protected hydroxyl-isoindoline-1,3-dione; and (v) deprotecting 4-amino-2-(2,6-dioxopiperidin-3-yl)-5-protected hydroxyl-isoindoline-1,3-dione, in one embodiment, by reacting with $BBr_3$, to 4-amino-2-(2,6-dioxopiperidin-3-yl)-5-hydroxyisoindoline-1,3-dione.

In still another embodiment, provided herein is a process for preparing 4-amino-2-(2,6-dioxopiperidin-3-yl)-5-hydroxyisoindoline-1,3-dione, or an enantiomer or a mixture of enantiomers thereof; or a pharmaceutically acceptable salt, solvate, hydrate, or polymorph thereof; comprising the steps of:

(i) reacting 1-nitro-naphthalen-2-ol with methyl iodide, in one embodiment, in the presence of a base, in another embodiment, in the presence of potassium carbonate, to form 2-methoxy-1-nitro-naphthalene;

(ii) oxidizing 2-methoxy-1-nitro-naphthalene with an oxidant, in one embodiment, a mixture of $RuO_4$ and $NaIO_4$, to form 4-methoxy-3-nitro-phthalic acid;

(iii) reacting 4-methoxy-3-nitro-phthalic acid with 3-aminopiperidine-2,6-dione, in one embodiment, in the presence of a coupling reagent, to form 2-(2,6-dioxopiperidin-3-yl)-5-methoxy-4-nitroisoindoline-1,3-dione;

(iv) reducing 2-(2,6-dioxopiperidin-3-yl)-5-methoxy-4-nitroisoindoline-1,3-dione to form 4-amino-2-(2,6-dioxopiperidin-3-yl)-5-methoxyisoindoline-1,3-dione; and (v) deprotecting 4-amino-2-(2,6-dioxopiperidin-3-yl)-5-methoxyisoindoline-1,3-dione, in one embodiment, by reacting with $BBr_3$, to 4-amino-2-(2,6-dioxopiperidin-3-yl)-5-hydroxyisoindoline-1,3-dione.

In still another embodiment, provided herein is a process for preparing an isoindoline-1,3-dione compound of Formula I:

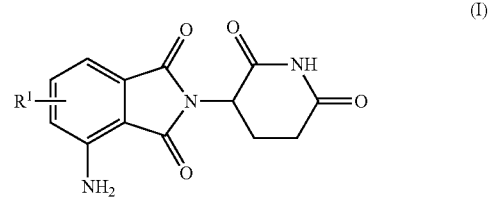

(I)

or an enantiomer or a mixture of enantiomers thereof; or a pharmaceutically acceptable salt, solvate, hydrate, or polymorph thereof;

comprising the step of converting the carboxyl group of a compound of Formula IV:

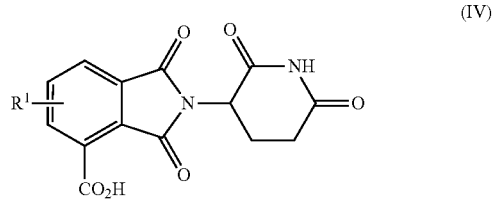

(IV)

to an amino group, thus to form the compound of Formula I; wherein $R^1$ is hydrogen, hydroxyl, or —$OR^{1a}$; and $R^{1a}$ is a hydroxyl protecting group.

In certain embodiments, the carboxyl-to-amino conversion is performed via the Schmidt rearrangement. In certain embodiments, the carboxyl-to-amino conversion is performed via the Curtius rearrangement. In certain embodiments, the Curtius rearrangement is performed with an azide compound. In certain embodiments, the azide compound is diphenylphosphoryl azide (DPPA).

In certain embodiments, the carboxyl-to-amino conversion is performed in the presence of a base. In certain embodiments, the base is an inorganic base. In certain embodiments, the base is an organic base. In certain embodiments, the base is triethylamine.

In certain embodiments, $R^1$ is hydrogen. In certain embodiments, $R^1$ is hydroxyl. In certain embodiments, $R^1$ is —$OR^{1a}$, wherein $R^{1a}$ is a hydroxyl protecting group. In certain embodiments, $R^{1a}$ is $C_{1-6}$ alkyl. In certain embodiments, $R^{1a}$ is methyl, ethyl, propyl, or t-butyl. In certain embodiments, $R^{1a}$ is methyl or isopropyl. In certain embodiments, $R^{1a}$ is methyl. In certain embodiments, $R^{1a}$ is isopropyl. In certain embodiments, $R^1$ is hydrogen, hydroxyl, methoxy, ethoxy, or isopropoxy. In certain embodiments, $R^1$ is hydrogen, hydroxyl, or isopropoxy. In certain embodiments, $R^1$ is hydroxyl or isopropoxy. In certain embodiments, $R^1$ is hydroxyl. In certain embodiments, $R^1$ is isopropoxy.

In certain embodiments, the compound of Formula IV is 2-(2,6-dioxo-piperidin-3-yl)-1,3-dioxo-2,3-dihydro-1H-isoindole-4-carboxylic acid, 2-(2,6-dioxo-piperidin-3-yl)-5-methoxy-1,3-dioxo-2,3-dihydro-1H-isoindole-4-carboxylic acid, 2-(2,6-dioxo-piperidin-3-yl)-6-methoxy-1,3-dioxo-2,3-dihydro-1H-isoindole-4-carboxylic acid, or 2-(2,6-dioxo-piperidin-3-yl)-7-methoxy-1,3-dioxo-2,3-dihydro-1H-isoindole-4-carboxylic acid; or an enantiomer or a mixture of enantiomers thereof. In certain embodiments, the compound of Formula IV is 2-(2,6-dioxo-piperidin-3-yl)-5-methoxy-1,3-dioxo-2,3-dihydro-1H-isoindole-4-carboxylic acid, 2-(2,6-dioxo-piperidin-3-yl)-6-methoxy-1,3-dioxo-2,3-dihydro-1H-isoindole-4-carboxylic acid, or 2-(2,6-dioxo-piperidin-3-yl)-7-methoxy-1,3-dioxo-2,3-dihydro-1H-isoindole-4-carboxylic acid; or an enantiomer or a mixture of enantiomers thereof. In certain embodiments, the compound of Formula IV is 2-(2,6-dioxo-piperidin-3-yl)-1,3-dioxo-2,3-dihydro-1H-isoindole-4-carboxylic acid, or an enantiomer or a mixture of enantiomers thereof. In certain embodiments, the compound of Formula IV is 2-(2,6-dioxo-piperidin-3-yl)-5-methoxy-1,3-dioxo-2,3-dihydro-1H-isoindole-4-carboxylic acid, or an enantiomer or a mixture of enantiomers thereof. In certain embodiments, the compound of Formula IV is 2-(2,6-dioxo-piperidin-3-yl)-6-methoxy-1,3-dioxo-2,3-dihydro-1H-isoindole-4-carboxylic acid, or an enantiomer or a mixture of enantiomers thereof. In certain embodiments, the compound of Formula IV is 2-(2,6-dioxo-piperidin-3-yl)-7-methoxy-1,3-dioxo-2,3-dihydro-1H-isoindole-4-carboxylic acid, or an enantiomer or a mixture of enantiomers thereof.

In certain embodiments, the compound of Formula I is 4-amino-2-(2,6-dioxo-piperidin-3-yl)-isoindole-1,3-dione, 4-amino-2-(2,6-dioxo-piperidin-3-yl)-5-hydroxy-isoindole-1,3-dione, 4-amino-2-(2,6-dioxo-piperidin-3-yl)-6-hydroxy-isoindole-1,3-dione, or 4-amino-2-(2,6-dioxo-piperidin-3-yl)-7-hydroxy-isoindole-1,3-dione; or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-5-hydroxy-isoindole-1,3-dione, 4-amino-2-(2,6-dioxo-piperidin-3-yl)-6-hydroxy-isoindole-1,3-dione, or 4-amino-2-(2,6-dioxo-piperidin-3-yl)-7-hydroxy-isoindole-1,3-dione; or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-5-hydroxy-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-6-hydroxy-isoindole-1,3-dione, or an enantiomer or a mixture of enantiomers thereof; or a pharmaceutically acceptable salt, solvate, hydrate, or polymorph thereof. In certain embodiments, the compound of Formula I is 4-amino-2-(2,6-dioxo-piperidin-3-yl)-7-hydroxy-isoindole-1,3-dione, or an enantiomer or a mixture of enantiomers thereof; or a pharmaceutically acceptable salt, solvate, hydrate, or polymorph thereof.

In certain embodiments, when $R^1$ is a protected hydroxyl, the process provided herein further comprises a step of removing the hydroxyl protecting group to form hydroxyl. In certain embodiments, the deprotection is performed with an acid. In certain embodiments, the acid is a Lewis acid. In certain embodiments, the acid is $AlCl_3$, $AlBr_3$, $BCl_3$, or $BBr_3$. In certain embodiments, the acid is $BCl_3$ or $BBr_3$.

In one embodiment, the process provided herein is for preparing 4-amino-2-(2,6-dioxopiperidin-3-yl)-6-hydroxy-isoindoline-1,3-dione:

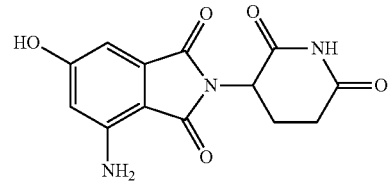 [SMILES: Nc1cc(O)cc2c1C(=O)N(C1CCC(=O)NC1=O)C2=O]

or an enantiomer or a mixture of enantiomers thereof; or a pharmaceutically acceptable salt, solvate, hydrate, or polymorph thereof; comprising the steps of:

(i) converting 2-(2,6-dioxo-piperidin-3-yl)-6-methoxy-1,3-dioxo-2,3-dihydro-1H-isoindole-4-carboxylic acid:

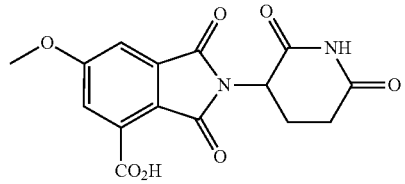 [SMILES: COc1cc(C(=O)O)c2c(c1)C(=O)N(C1CCC(=O)NC1=O)C2=O]

to 4-amino-2-(2,6-dioxo-piperidin-3-yl)-6-methoxy-isoindole-1,3-dione:

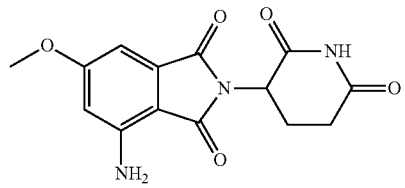

in one embodiment, via the Curtius rearrangement, in another embodiment, by reacting with an azide compound, in yet another embodiment, by reacting with DPPA; and (ii) deprotecting 4-amino-2-(2,6-dioxo-piperidin-3-yl)-6-methoxy-isoindole-1,3-dione, in one embodiment, with $BBr_3$, to form 4-amino-2-(2,6-dioxopiperidin-3-yl)-6-hydroxyisoindoline-1,3-dione.

In another embodiment, the process provided herein is for preparing 4-amino-2-(2,6-dioxopiperidin-3-yl)-6-hydroxyisoindoline-1,3-dione, or an enantiomer or a mixture of enantiomers thereof; or a pharmaceutically acceptable salt, solvate, hydrate, or polymorph thereof; comprising the steps of:

(i) reacting 2-(2,6-dioxo-piperidin-3-yl)-6-methoxy-1,3-dioxo-2,3-dihydro-1H-isoindole-4-carboxylic acid with (a) an azide compound, in one embodiment, DPPA; in the presence of (b) a base, in one embodiment, an organic base, in another embodiment, triethylamine; to form 4-amino-2-(2,6-dioxo-piperidin-3-yl)-6-methoxy-isoindole-1,3-dione; and (ii) reacting 4-amino-2-(2,6-dioxo-piperidin-3-yl)-6-methoxy-isoindole-1,3-dione with a deprotecting reagent, in one embodiment, $BBr_3$, to form 4-amino-2-(2,6-dioxopiperidin-3-yl)-6-hydroxyisoindoline-1,3-dione.

In one embodiment, the process for preparing 4-amino-2-(2,6-dioxopiperidin-3-yl)-6-hydroxyisoindoline-1,3-dione further comprises a process for preparing 2-(2,6-dioxo-piperidin-3-yl)-6-methoxy-1,3-dioxo-2,3-dihydro-1H-isoindole-4-carboxylic acid, which comprises the step of reacting 5-methoxy-benzene-1,2,3-tricarboxylic acid with 3-aminopiperidine-2,6-dione to form 2-(2,6-dioxo-piperidin-3-yl)-6-methoxy-1,3-dioxo-2,3-dihydro-1H-isoindole-4-carboxylic acid; wherein the methyl group functions as a hydroxyl protecting group. Thus, other suitable hydroxyl protecting groups can also be used in the place of the methyl group. In certain embodiments, the hydroxyl protecting group is methyl, ethyl, isopropyl, benzyl, or a silyl group. In certain embodiments, the hydroxyl protecting group is methyl, ethyl, isopropyl, or benzyl. In certain embodiments, the hydroxyl protecting group is methyl or isopropyl. In certain embodiments, the hydroxyl protecting group is methyl. In certain embodiments, the hydroxyl protecting group is isopropyl.

In certain embodiments, the coupling reaction (i.e., the reaction of 5-methoxy-benzene-1,2,3-tricarboxylic acid with 3-aminopiperidine-2,6-dione) is performed in the presence of a coupling reagent. In certain embodiments, the coupling reagent is an anhydride. In certain embodiments, the coupling reagent is acetic anhydride. In certain embodiments, the coupling reagent is CDI or EDCI.

In another embodiment, the process for preparing 4-amino-2-(2,6-dioxopiperidin-3-yl)-6-hydroxyisoindoline-1,3-dione further comprises a process for preparing 5-methoxy-benzene-1,2,3-tricarboxylic acid, which comprises the step of reacting 4-methoxy-2,6-dimethyl-benzaldehyde with an oxidant, in one embodiment, $KMnO_4$, to form 5-methoxy-benzene-1,2,3-tricarboxylic acid; wherein the methyl group of the methoxy group functions as a hydroxyl protecting group. Thus, other suitable hydroxyl protecting groups can also be used in the place of the methyl group. In certain embodiments, the hydroxyl protecting group is methyl, ethyl, isopropyl, benzyl, or a silyl group. In certain embodiments, the hydroxyl protecting group is methyl, ethyl, isopropyl, or benzyl. In certain embodiments, the hydroxyl protecting group is methyl or isopropyl. In certain embodiments, the hydroxyl protecting group is methyl. In certain embodiments, the hydroxyl protecting group is isopropyl.

In yet another embodiment, the process provided herein for preparing 4-amino-2-(2,6-dioxopiperidin-3-yl)-6-hydroxyisoindoline-1,3-dione comprises the steps of:

(i) reacting 4-protected hydroxyl-2,6-dimethyl-benzaldehyde with an oxidant to form a 5-protected hydroxyl-benzene-1,2,3-tricarboxylic acid;

(ii) reacting the 5-protected hydroxyl-benzene-1,2,3-tricarboxylic acid with 3-aminopiperidine-2,6-dione to form a 2-(2,6-dioxo-piperidin-3-yl)-6-protected hydroxyl-1,3-dioxo-2,3-dihydro-1H-isoindole-4-carboxylic acid;

(iii) reacting the 2-(2,6-dioxo-piperidin-3-yl)-6-protected hydroxyl-1,3-dioxo-2,3-dihydro-1H-isoindole-4-carboxylic acid with an azide compound to form a 4-amino-2-(2,6-dioxo-piperidin-3-yl)-6-protected hydroxyl-isoindole-1,3-dione; and (iv) deprotecting the 4-amino-2-(2,6-dioxo-piperidin-3-yl)-6-protected hydroxyl-isoindole-1,3-dione to form 4-amino-2-(2,6-dioxopiperidin-3-yl)-6-hydroxyisoindoline-1,3-dione.

In still another embodiment, the process for preparing 4-amino-2-(2,6-dioxopiperidin-3-yl)-6-hydroxyisoindoline-1,3-dione comprises the steps of:

(i) reacting 4-methoxy-2,6-dimethyl-benzaldehyde with an oxidant, in one embodiment, $KMnO_4$, to form 5-methoxy-benzene-1,2,3-tricarboxylic acid;

(ii) reacting 5-methoxy-benzene-1,2,3-tricarboxylic acid with 3-aminopiperidine-2,6-dione, in one embodiment, in the presence of a coupling reagent, to form 2-(2,6-dioxo-piperidin-3-yl)-6-methoxy-1,3-dioxo-2,3-dihydro-1H-isoindole-4-carboxylic acid;

(iii) converting 2-(2,6-dioxo-piperidin-3-yl)-6-methoxy-1,3-dioxo-2,3-dihydro-1H-isoindole-4-carboxylic acid to 4-amino-2-(2,6-dioxo-piperidin-3-yl)-6-methoxy-isoindole-1,3-dione, in one embodiment, via the Curtius rearrangement, in another embodiment, by reacting with an azide compound, in yet another embodiment, with DPPA; and (iv) reacting 4-amino-2-(2,6-dioxo-piperidin-3-yl)-6-methoxy-isoindole-1,3-dione with a deprotecting reagent, in one embodiment, $BBr_3$, to form 4-amino-2-(2,6-dioxopiperidin-3-yl)-6-hydroxyisoindoline-1,3-dione.

VI. EXAMPLES

Certain embodiments are illustrated by the following non-limiting examples.

In the examples below, unless otherwise indicated, all temperatures are in Celsius and all parts and percentages are by weight. Reagents may be purchased from commercial suppliers, e.g., Sigma-Aldrich® Chemical Co., and may be used without further purification unless otherwise indicated. Reagents may also be prepared following standard literature procedures known to those skilled in the art. Solvents may be used as received or may be purified using standard methods known to those skilled in the art, unless otherwise indicated.

Unless otherwise specified, the reactions set forth below were done at ambient or room temperature. Reactions were monitored with TLC, LCMS or HPLC, and terminated as judged by the consumption of a starting material.

The compound structures and purities in the examples below were confirmed by one or more of the following methods: proton nuclear magnetic resonance ($^1$H NMR) spectroscopy, $^{13}$C NMR spectroscopy, mass spectroscopy, infrared spectroscopy, melting point, X-ray crystallography, and/or HPLC. $^1$H NMR spectra were determined using a NMR spectrometer. Chemical shifts are reported in parts per million (ppm, δ) downfield from a standard, e.g., an internal standard, such as TMS. Alternatively, $^1$H NMR spectra were referenced to signals from residual proton(s) in a deuterated solvent as follows: $CDCl_3$=7.25 ppm; $DMSO_{d6}$=2.49 ppm; $C_6D_6$=7.16 ppm; and $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

Example 1

Preparation of 4-amino-2-(2,6-dioxopiperidin-3-yl)-5-hydroxyisoindoline-1,3-dione 1

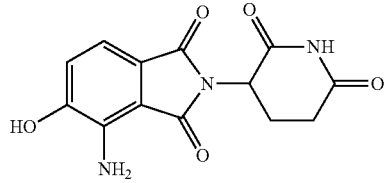

The synthesis of compound 1 is exemplified in Scheme 1.

Preparation of dimethyl 4-hydroxyphthalate C1-2

To a solution of 4-hydroxyphthalic acid (20 g, 110 mmol) in $CH_3OH$ (100 mL) was added $SOCl_2$ (20 mL). The resulting solution was stirred at 80° C. for 4 hrs. The volatile was removed in vacuo to yield compound C1-2 as a white solid (23 g, yield: 99%), which was used directly in the next step without further purification. $^1H$ NMR ($CDCl_3$, 400 MHz) δ: 7.77 (d, J=8.8 Hz, 1H), 7.03 (d, J=2 Hz, 1H), 6.95 (dd, J=8.4 and 2.0 Hz, 1H), 3.93 (s, 3H), 3.88 (s, 3H); MS (ESI⁺): m/z 211(M+1).

Scheme 1

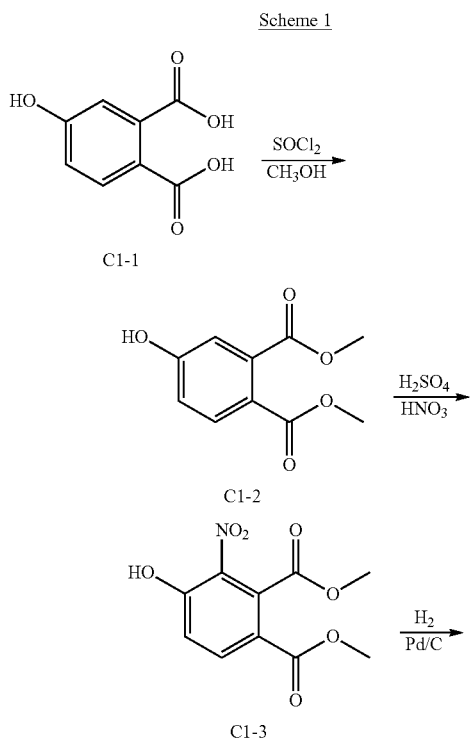

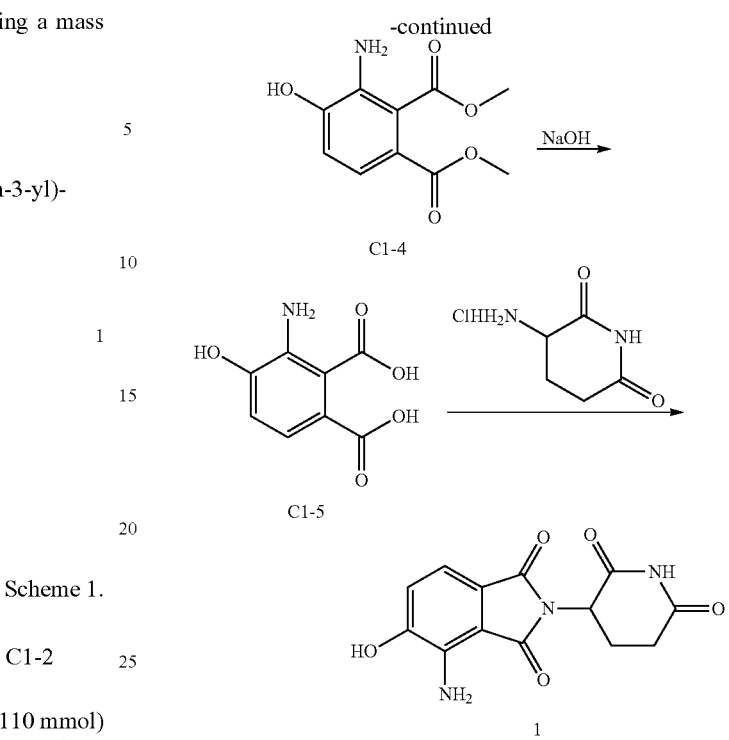

Preparation of dimethyl 4-hydroxy-3-nitrophthalate C1-3

To a stirred solution of dimethyl 4-hydroxyphthalate C1-2 (21 g, 100 mmol) in $H_2SO_4$ (100 mL) in an ice-water bath was added $HNO_3$ (6.3 g) dropwise. The reaction mixture was then stirred at room temperature for 2 hrs. LCMS showed that the reaction was complete. The mixture was poured into ice-water (300 mL). The solution was extracted with ethyl acetate (500 mL×4). The combined organic layers were dried over $Na_2SO_4$, filtered, and concentrated to yield a yellow solid (26.4 g, yield: 95%), which contained compound C1-3 and dimethyl 4-hydroxy-5-nitrophthalate) in a ratio of 6:4. The mixture was used directly in the next step without further purification. $^1H$ NMR ($CD_3OD$, 400 MHz) δ: (d, J=8.8 Hz, 1H), 7.18 (d, J=8.8 Hz, 1H), 3.88 (s, 3H), 3.87 (s, 3H); MS (ESI⁺): m/z 256 (M+1).

Preparation of dimethyl 3-amino-4-hydroxyphthalate C1-4

A mixture of the crude dimethyl 4-hydroxy-3-nitrophthalate C1-3 (25 g, 98 mmol) and Pd/C (1.0 g) in $CH_3OH$ (400 mL) was stirred at room temperature overnight under $H_2$ atmosphere. LCMS showed that the reaction was complete. The reaction mixture was filtered through a celite pad and the filtrate was evaporated in vacuo. The residue was purified by chromatography (silica gel, PE:EA (1:1, v:v)) to yield compound C1-4 as a yellow solid (11.5 g, yield: 52%). $^1H$ NMR (DMSO-$d_6$, 400 MHz) δ: 10.45 (s, 1H), 6.89 (d, J=8 Hz, 1H), 6.37 (d, J=8 Hz, 1H), 5.19 (s, 2H), 3.75 (s, 3H), 3.72 (s, 3H); MS (ESI⁺): m/z 226 (M+1).

Preparation of 3-amino-4-hydroxyphthalic acid C1-5

A solution of dimethyl 3-amino-4-hydroxyphthalate C1-4 (11.25 g, 50 mmol) and NaOH (14.0 g, 350 mmol) in ethanol (140 mL) and H₂O (50 mL) was stirred at 70° C. overnight. LCMS indicated that the reaction was complete. The reaction mixture was concentrated in vacuo, neutralized to pH<3, and filtered to yield 3-amino-4-hydroxyphthalic acid C1-5 as a white solid (9.6 g, yield: 97%), which was used directly in the next step without further purification.

Preparation of 4-amino-2-(2,6-dioxopiperidin-3-yl)-5-hydroxyisoindoline-1,3-dione 1

3-Aminopiperidine-2,6-dione hydrochloride (9.58 g, 58.4 mmol) was dissolved in triethylamine (TEA) (14.7 g) and the mixture was stirred at room temperature for 4 hrs. HOAc (150 mL) and 3-amino-4-hydroxyphthalic acid C1-5 (9.6 g, 48.7 mmol) were added. The mixture was stirred at 120° C. for 20 mins. TEA was added until the white solid was dissolved completely. The mixture was stirred at 120° C. for 2 hrs. After cooling, the solution was extracted with ethyl acetate (500 mL×4). The combined organic layers were dried over Na₂SO₄, filtered, and concentrated to a dark solid. The dark solid was washed with EA (300 mL) and dried to give compound 1 as a dark solid (7.2 g, yield: 51%). ¹H NMR (DMSO-d₆, 400 MHz) δ: 11.05 (s, 1H), 10.82 (s, 1H), 6.98 (d, J=8 Hz, 1H), 6.92 (d, J=7.6 Hz, 1H), 5.95 (s, 2H), 5.03-4.98 (m, 1H), 2.91-2.83 (m, 1H), 2.60-2.44 (m, 2H), 2.01-1.98 (m, 1H); MS (ESI⁺): m/z 290 (M+1); Elem. Anal. Calcd. for C₁₃H₁₁N₃O₅: C, 53.98; H, 3.83; N, 14.53. Found: C, 53.67; H, 3.80; N, 14.44.

Example 2

Preparation of 4-amino-2-(2,6-dioxopiperidin-3-yl)-6-hydroxyisoindoline-1,3-dione 2

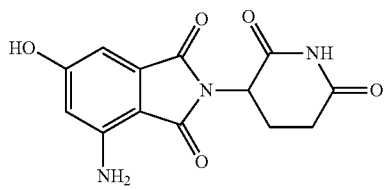

The synthesis of compound 2 is exemplified in Scheme 2.

Preparation of 5-bromo-2-methyl-3-nitrobenzoic acid C2-1

To a mixture of compound C2-0 (15 g, 82.8 mmol) in conc. H₂SO₄ (60 mL) in an ice-water bath was added 1,3-dibromo-5,5-dimethylhydantoin (DBDMH) (13.4 g, 46.8 mmol) portionwise over 30 mins. After the mixture was stirred at room temperature overnight, the reaction mixture was added slowly to ice-water (400 mL). The precipitation was collected and dried to yield compound C2-1 as a white solid ((21.2 g, yield: 98%), which was used directly in the next step without further purification. MS (ESI⁻): m/z 257.9 and 259.9 (M-1).

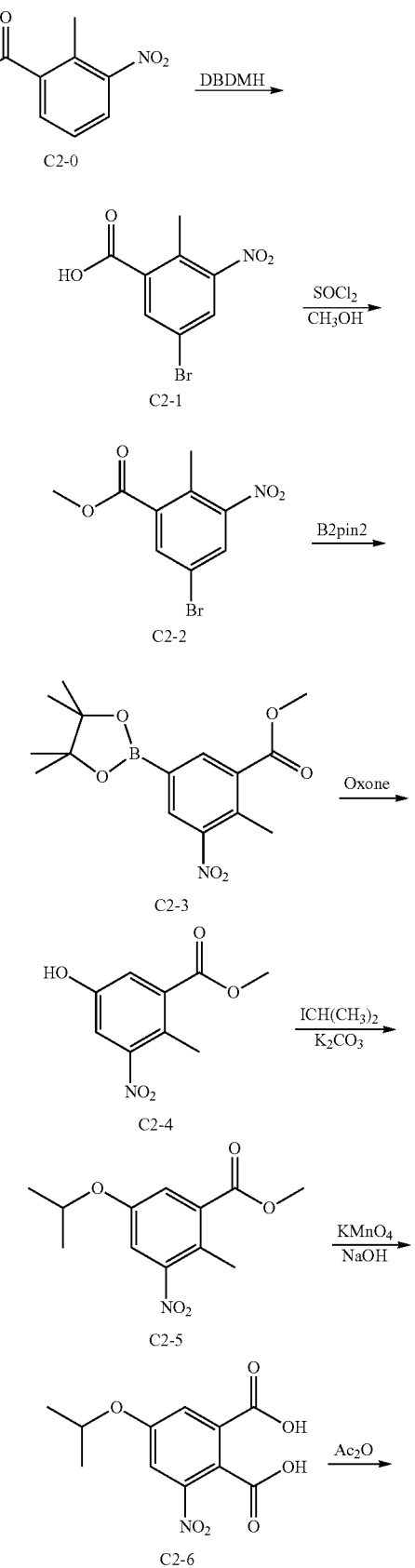

Scheme 2

-continued

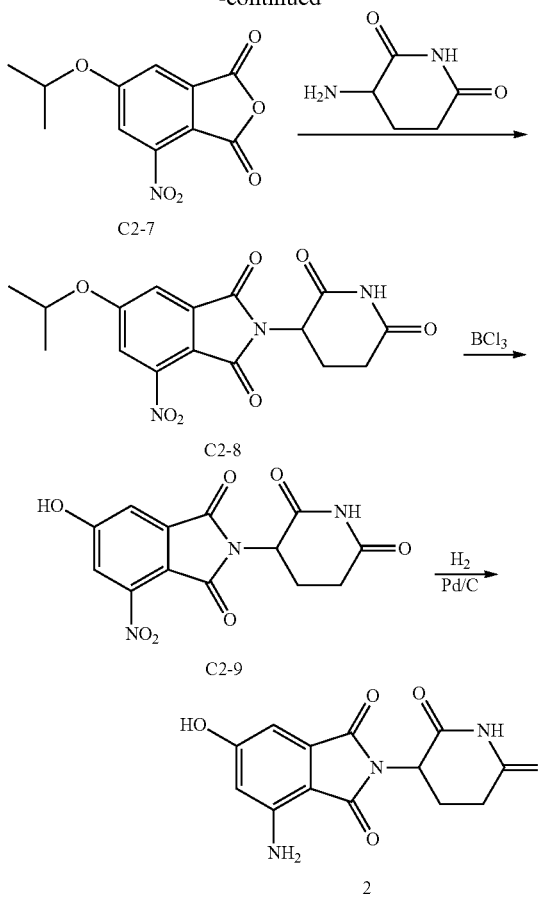

Preparation of methyl 5-bromo-2-methyl-3-nitrobenzoate C2-2

A mixture of 5-bromo-2-methyl-3-nitrobenzoic acid C2-1 (21.2 g, 81.5 mmol) in $SOCl_2$ (100 mL) was heated to reflux until the mixture became clear (about 1.5 hrs). The reaction mixture was cooled and concentrated in vacuo. The residue was added portionwise to 250 mL of MeOH. The resulting mixture was stirred overnight under refluxing. The reaction mixture was cooled and concentrated. The residue was dissolved in 300 mL of EA, washed sequentially with sat. aq. $NaHCO_3$ and brine, dried over $MgSO_4$, and concentrated. The residue was purified by chromatography (silica gel, PE:EA (20:1, v:v)) to yield compound C2-2 as a light yellow solid (21.2 g, yield: 95%).

Preparation of methyl 2-methyl-3-nitro-5-(4,4,5,5-tetramethyl-1,3,2-dioxaborolan-2-yl)benzoate C2-3

A mixture of compound C2-2 (25.4 g, 92.5 mmol), bis(pinacolato)diboron (B2pin2) (24.0 g, 93 mmol), KOAc (18.0 g, 185 mmol), and $Pd(dppf)Cl_2$ (1.0 g) in dioxane (250 mL) was refluxed overnight under $N_2$ atmosphere. The reaction mixture was then cooled and concentrated. The residue was purified by chromatography (silica gel, PE:EA (5:1, v:v)) to yield compound C2-3 as a mixture of boric acid and pinacol ester (21.8 g), which was used directly in the next step without further purification.

Preparation of methyl 5-hydroxy-2-methyl-3-nitrobenzoate C2-4

To a solution of compound C2-3 (24.2 g, 68.5 mmol) in acetone (250 mL) in an ice-water bath was added sat. aq. OXONE® (100 mL) with vigorous stirring. The mixture was stirred for another 1 hr at room temperature. The reaction was then quenched with sat. aq. $NaHSO_3$. The mixture was concentrated in vacuo and extracted with EA. The combined organic layers were washed with brine, dried over $MgSO_4$, concentrated, and purified by reversed phase chromatography to yield compound C2-4 as a grey-white solid (11.2 g, yield: 78%). $^1H$ NMR ($CDCl_3$, 400 MHz) δ: 7.42 (d, J=2.4 Hz, 1H), 7.37 (d, J=2.4 Hz, 1H), 3.94 (s, 3H), 2.50 (s, 3H); MS ($ESI^+$): m/z 212 (M+1).

Preparation of methyl 5-isopropoxy-2-methyl-3-nitrobenzoate C2-5

To a solution of compound C2-4 (22.0 g, 100 mmol) in $CH_3CN$ (300 mL) was added $K_2CO_3$ (27.6 g, 200 mmol), followed by addition of 2-iodopropane (15 mL, 120 mmol). The mixture was then refluxed overnight. The mixture was filtered, and the filtrate was concentrated and purified by chromatography (silica gel, PE:EA (15:1, v:v)) to yield compound C2-5 as a yellow oil (22.5 g, yield: 89%). MS ($ESI^+$): m/z 254 (M+1).

Preparation of 5-isopropoxy-3-nitrophthalic acid C2-6

To a solution of compound C2-5 (10.0 g, 50 mmol) in $H_2O$ (100 mL) was added NaOH (6 g, 0.15 mol). The reaction was heated until clear and $KMnO_4$ was added slowly in portions. The reaction mixture was stirred at 100° C. for 2 hours. The reaction mixture was stirred at 100° C. for 2 hrs. The mixture was cooled and filtered. The filtrate was acidified to pH 4 and extracted with EtOAc (100 mL×3). The combined organic layers were dried and concentrated to yield compound C2-6 (1.7 g, yield: 15%). MS ($ESI^+$): m/z 269 (M+1).

Preparation of 6-isopropoxy-4-nitroisobenzofuran-1,3-dione C2-7

A mixture of compound C2-6 (1.7 g, 6.3 mmol) and acetic anhydride (20 mL) was stirred at 130° C. for 2 hrs under $N_2$ atmosphere. The reaction mixture was cooled and concentrated to provide compound C2-7 as an oil (1.3 g, yield: 82%), which was used directly in the next step without further purification. MS ($ESI^+$): m/z 251 (M+1).

Preparation of 2-(2,6-dioxopiperidin-3-yl)-6-isopropoxy-4-nitroisoindoline-1,3-dione C2-8

To a solution of compound C2-7 (1.3 g, 5.1 mmol) in AcOH (10 mL) was added 3-aminopiperidine-2,6-dione (0.66 g, 5.1 mmol). The reaction mixture was stirred at 100° C. for 4 hrs. The mixture was then cooled and concentrated to give compound C2-8 (1.0 g, yield: 54%). MS ($ESI^+$): m/z 361 (M+1).

Preparation of 2-(2,6-dioxopiperidin-3-yl)-6-hydroxy-4-nitroisoindoline-1,3-dione C2-9

To a solution of compound C2-8 (1.0 g, 2.7 mmol) in DCM (20 mL) was added $BCl_3$ (27 mL, 27 mmol). The reaction mixture was stirred at room temperature for 12 hrs. The reaction was quenched by adding DCM (10 mL) and $H_2O$ (20 mL). The organic layer was separated, filtered, and concentrated to yield compound C2-9 (0.7 g, yield: 81%). MS (ESI⁺): m/z 319 (M+1).

Preparation of 4-amino-2-(2,6-dioxopiperidin-3-yl)-6-hydroxyisoindoline-1,3-dione 2

A mixture of compound C2-9 (0.7 g, 2.2 mmol) and Pd/C (70 mg) in THF (20 mL) was stirred in hydrogen atmosphere at ambient pressure and 25° C. for 30 min. The mixture was filtered through a plug of celite and washed with EtOAc (20 mL). The organic phase was dried, concentrated, and purified by pre-HPLC (water (0.1% TFA): ACN) to yield compound 2 (0.3 g, yield: 47.0%, purity: >99%). $^1$H NMR (DMSO-d6, 300 MHz) δ: 11.05 (s, 1H), 10.58 (br, 1H), 6.42 (d, J=1.8 Hz, 1H), 6.35-6.31 (m, 3H), 4.97 (dd, J=12.6, 5.7 Hz, 1H), 2.87 (ddd, J=19.2, 13.8, 5.1 Hz, 1H), 2.59-2.42 (m, 2H), 2.01-1.94 (m, 1H); MS (ESI+): m/z 290 (M+1).

Example 3

Preparation of 4-amino-2-(2,6-dioxopiperidin-3-yl)-7-hydroxyisoindoline-1,3-dione 3

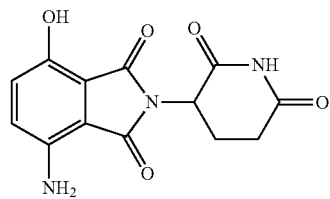

The synthesis of compound 3 is exemplified in Scheme 3.

Scheme 3

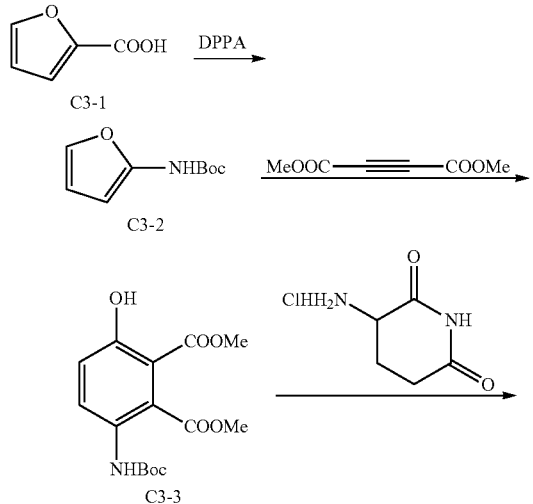

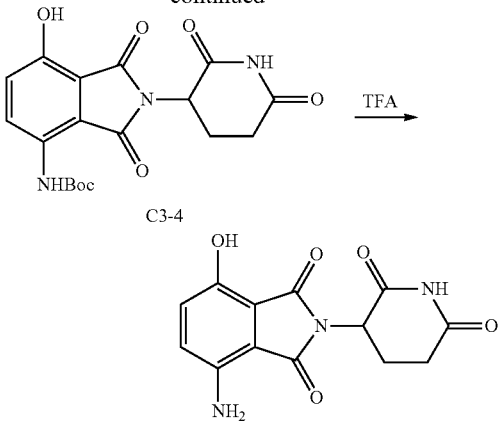

Preparation of tert-butyl furan-2-ylcarbamate C3-2

A solution of furan-2-carboxylic acid (35.0 g, 312.2 mmol), triethylamine (86 mL, 624.5 mmol), and diphenyl phosphorazidate (DPPA) (135 mL, 624.5 mmol) in tert-butyl alcohol (400 mL) was refluxed overnight. The volatile was removed in vacuo and the residue was purified by chromatography (silica gel, PE to EA:PE (1:30, v:v)) to give compound $C_{3-2}$ as a white solid (55.0 g, yield: 96%). $^1$H NMR (DMSO-d$_6$, 400 MHz) δ: 1.43 (s, 9H), 5.91 (s, 1H), 6.37 (t, J=2.6 Hz, 1H), 7.26 (s, 1H), 9.81 (s, 1H).

Preparation of dimethyl 3-(tert-butoxycarbonylamino)-6-hydroxyphthalate C3-3

A solution of tert-butyl furan-2-ylcarbamate C3-2 (55.0 g, 300.2 mmol) and dimethyl but-2-ynedioate (73.5 mL, 600.4 mmol) in toluene (100 mL) was heated at 45° C. for 4 hrs. The solvent was removed in vacuo and the residue was purified by chromatography (silica gel, PE to EA:PE (1:20, v:v)) to give compound $C_{3-2}$ as a light yellow solid (36.1 g, yield: 37%). $^1$H NMR (DMSO-d$_6$, 400 MHz) δ: 1.41 (s, 9H), 3.69 (s, 3H), 3.73 (s, 3H), 7.02 (d, J=8.8 Hz, 1H), 7.35 (d, J=9.2 Hz, 1H), 8.93 (s, 1H), 10.07 (s, 1H); MS (ESI+): m/z 238 (M-87).

Preparation of tert-butyl 2-(2,6-dioxopiperidin-3-yl)-7-hydroxy-1,3-dioxoisoindolin-4-ylcarbamate C3-4

A solution of dimethyl 3-(tert-butoxycarbonylamino)-6-hydroxyphthalate C3-3 (7.68 g, 23.6 mmol) and 3-aminopiperidine-2,6-dione hydrochloride (7.77 g, 47.2 mmol) in pyridine (150 mL) was heated at 100° C. overnight. The solvent was removed in vacuo and the residue was purified by chromatography (silica gel, DCM:MeOH:PE) to give compound C3-4 as a yellow solid (6.73 g, yield: 73%). $^1$H NMR (DMSO-d$_6$, 400 MHz) δ: 1.47 (s, 9H), 1.98-2.02 (m, 1H), 2.54-2.60 (m, 2H), 2.83-2.92 (m, 1H), 5.04 (dd, J=13.0 and 5.4 Hz, 1H), 7.22 (d, J=8.8 Hz, 1H), 8.10 (d, J=9.2 Hz, 1H), 8.68 (s, 1H), 11.01 (s, 1H), 11.11 (s, 1H); MS (ESI+): m/z 412 (M+23).

Preparation of 4-amino-2-(2,6-dioxopiperidin-3-yl)-7-hydroxyisoindoline-1,3-dione 3

To a solution of 2-(2,6-dioxopiperidin-3-yl)-7-hydroxy-1,3-dioxoisoindolin-4-ylcarbamate $C_{3-4}$ (6.73 g, 17.2 mmol) in DCM (200 mL) was added TFA (20 mL) slowly. The mixture was stirred at room temperature overnight. Water (20 mL) was added to quench the reaction. The mixture was extracted with EA (100 mL×3). The combined organic layers were collected and dried over $Na_2SO_4$, filtered, and concentrated. The residue was purified by chromatography (silica gel, DCM:MeOH:PE) to give 4-amino-2-(2,6-dioxopiperidin-3-yl)-7-hydroxyisoindoline-1,3-dione 3 as a yellow solid (4.05 g, yield: 81%). $^1$H NMR (DMSO$_{d6}$, 400 MHz) δ: 1.95-1.98 (m, 1H), 2.52-2.58 (m, 2H), 2.83-2.92 (m, 1H), 4.98 (dd, J=12.6, 5.4 Hz, 1H), 6.06 (s, 2H), 6.95 (d, J=8.8 Hz, 1H), 7.06 (d, J=9.2 Hz, 1H), 10.17 (s, 1H), 11.05 (s, 1H); MS (ESI+): m/z 290 (M+1); Elem. Anal. Calcd. for $C_{13}H_{11}N_3O_5$: C, 53.98; H, 3.83; N, 14.53. Found C, 53.96; H, 3.74; N, 14.45.

Example 4

Preparation of 4-amino-2-(2,6-dioxopiperidin-3-yl)-5-hydroxyisoindoline-1,3-dione 1

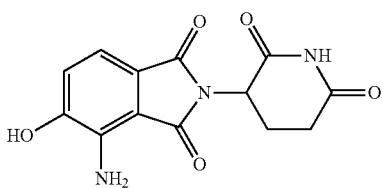

1

The synthesis of compound 1 is exemplified in Scheme 4.

Scheme 4

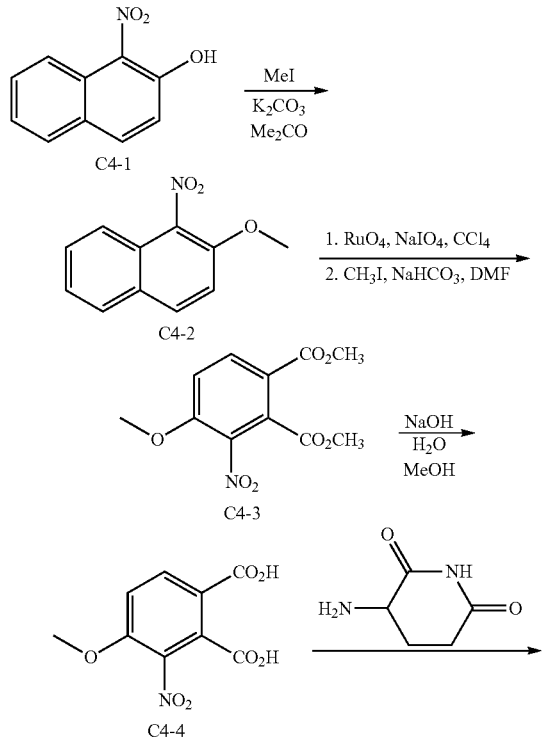

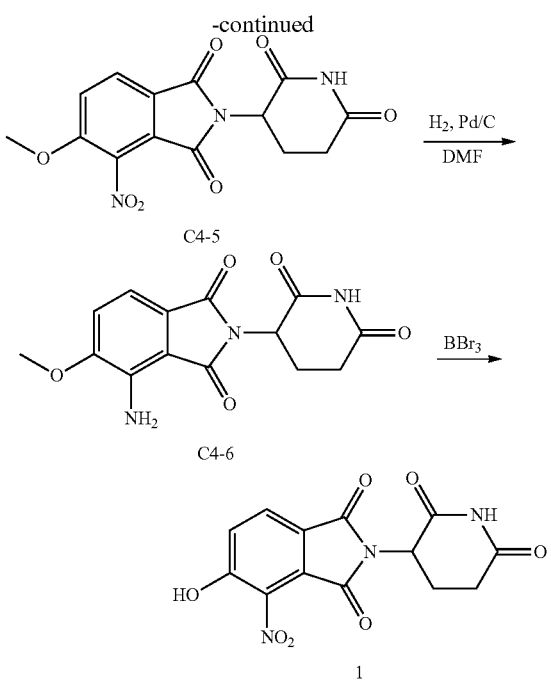

The reaction of 1-nitro-naphthalen-2-ol C4-1 with methyl iodide in the presence of a base, e.g., potassium carbonate, forms 2-methoxy-1-nitro-naphthalene C4-2. The oxidation of compound C4-2 with an oxidant, e.g., a mixture of $RuO_4$ and $NaIO_4$, followed by the reaction with methyl iodide, leads to the formation of 4-methoxy-3-nitro-phthalic acid dimethyl ester C4-3. The hydrolysis of compound C4-3 leads to the formation of 4-methoxy-3-nitro-phthalic acid C4-4. The coupling of compound C4-4 with 3-aminopiperidine-2,6-dione forms 2-(2,6-dioxo-piperidin-3-yl)-5-methoxy-4-nitro-isoindole-1,3-dione C4-5. The reduction of compound C4-5 with a reducing agent, e.g., hydrogen, leads to the formation of 4-amino-2-(2,6-dioxo-piperidin-3-yl)-5-methoxy-isoindole-1,3-dione C4-6. The deprotection of the hydroxyl protecting group (Me) of compound C4-6 with a deprotecting agent, e.g., $BBr_3$, leads to the formation of 4-amino-2-(2,6-dioxopiperidin-3-yl)-5-hydroxyisoindoline-1,3-dione 1.

Example 5

Preparation of 4-amino-2-(2,6-dioxopiperidin-3-yl)-6-hydroxyisoindoline-1,3-dione 2

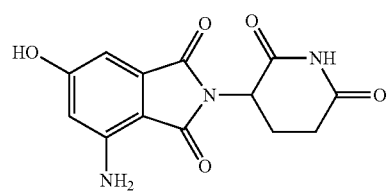

2

The synthesis of compound 2 is exemplified in Scheme 5.

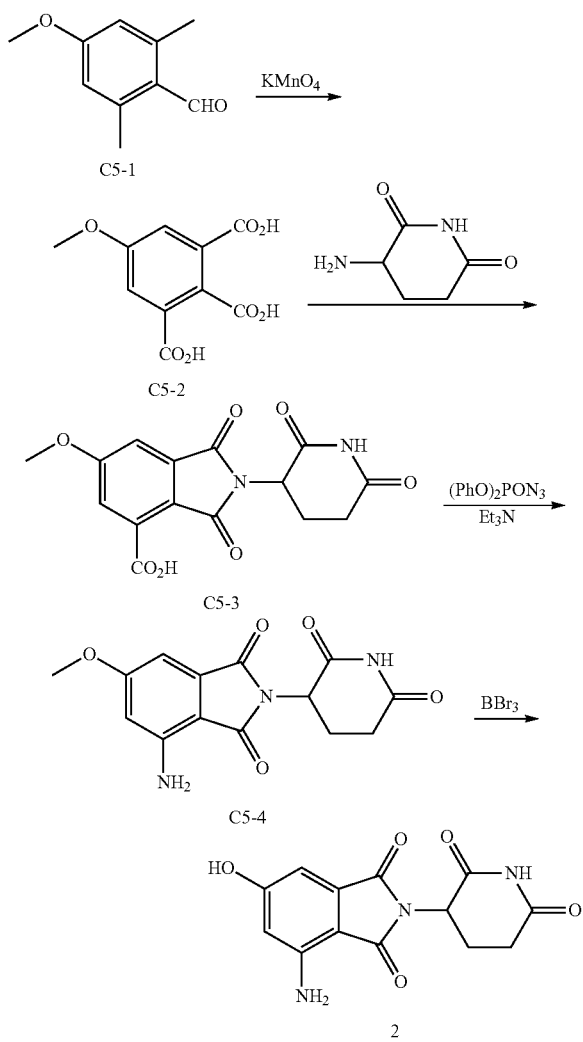

The oxidation of 4-methoxy-2,6-dimethyl-benzaldehyde C5-1 with an oxidant, e.g., KMnO$_4$, forms 5-methoxy-benzene-1,2,3-tricarboxylic acid C$_{5-2}$. See Djerassi *J. Am. Chem. Soc.* 1946, 68, 1862. The coupling of compound C5-2 with 3-aminopiperidine-2,6-dione forms 2-(2,6-dioxo-piperidin-3-yl)-6-methoxy-1,3-dioxo-2,3-dihydro-1H-isoindole-4-carboxylic acid C5-3. The reaction of compound C5-3 with diphenylphosphoryl azide leads to the formation of 4-amino-2-(2,6-dioxo-piperidin-3-yl)-6-methoxy-isoindole-1,3-dione C5-4. The deprotection of the hydroxyl protecting group (Me) of compound C5-4 with a deprotecting agent, e.g., BBr$_3$, leads to the formation of 4-amino-2-(2,6-dioxopiperidin-3-yl)-6-hydroxyisoindoline-1,3-dione 2.

The embodiments described herein are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

All of the patents, patent applications and publications referred to herein are each incorporated herein by reference in its entirety. Citation or identification of any reference in this application is not an admission that such a reference is available as prior art to this application. The full scope of the disclosure is better understood with reference to the appended claims.

What is claimed:

1. A process for preparing a compound of Formula I:

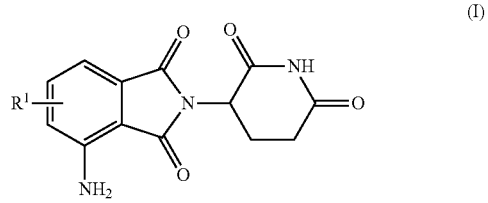

or an enantiomer or a mixture of enantiomers thereof; or a pharmaceutically acceptable salt thereof;
comprising the step of reacting a compound of Formula Ia:

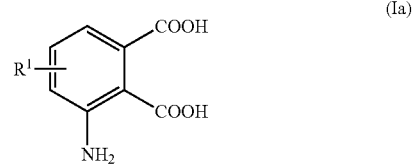

with 3-aminopiperidine-2,6-dione, or an enantiomer or a mixture of enantiomers thereof; or a salt thereof, in the presence of triethylamine; to form the compound of Formula I;
wherein R$^1$ is hydroxyl.

2. The process of claim 1, wherein the compound of Formula I is 4-amino-2-(2,6-dioxo-piperidin-3-yl)-5-hydroxy-isoindole-1,3-dione, 4-amino-2-(2,6-dioxo-piperidin-3-yl)-6-hydroxy-isoindole-1,3-dione, or 4-amino-2-(2,6-dioxo-piperidin-3-yl)-7-hydroxy-isoindole-1,3-dione; or an enantiomer or a mixture of enantiomers thereof or a pharmaceutically acceptable salt thereof.

3. The process of claim 1, wherein the compound of Formula I is 4-amino-2-(2,6-dioxo-piperidin-3-yl)-5-hydroxy-isoindole-1,3-dione, or an enantiomer or a mixture of enantiomers thereof; or a pharmaceutically acceptable salt thereof.

4. The process of claim 1, wherein the compound of Formula I is 4-amino-2-(2,6-dioxo-piperidin-3-yl)-6-hydroxy-isoindole-1,3-dione, or an enantiomer or a mixture of enantiomers thereof; or a pharmaceutically acceptable salt thereof.

5. The process of claim 1, wherein the compound of Formula I is 4-amino-2-(2,6-dioxo-piperidin-3-yl)-7-hydroxy-isoindole-1,3-dione, or an enantiomer or a mixture of enantiomers thereof; or a pharmaceutically acceptable salt thereof.

6. The process of claim 1, wherein the compound of Formula Ia is 3-amino-4-hydroxy-phthalic acid, 3-amino-5-hydroxy-phthalic acid, or 3-amino-6-hydroxy-phthalic acid.

7. The process of claim 1, wherein the reaction is performed in the presence of a coupling reagent.

8. The process of claim 1, wherein the reaction is performed in the presence of an acid.

9. The process of claim 8, wherein the acid is acetic acid.

10. The process of claim 1, wherein the reaction is performed at an elevated temperature ranging from about 30 to about 200° C.

11. The process of claim 3, further comprising the steps of:
(i) protecting 4-hydroxyphthalic acid with a carboxyl protecting group to form a carboxyl protected 4-hydroxyphthalic acid;
(ii) reacting the carboxyl protected 4-hydroxyphthalic acid with a nitration reagent to form a carboxyl protected 4-hydroxy-3-nitrophthalic acid;
(iii) reducing the carboxyl protected 4-hydroxy-3-nitrophthalic acid to form a carboxyl protected 3-amino-4-hydroxyphthalic acid; and
(iv) deprotecting the carboxyl protected 3-amino-4-hydroxyphthalic acid to form 3-amino-4-hydroxyphthalic acid.

* * * * *